US012251423B2

(12) United States Patent
Schrattenholz

(10) Patent No.: US 12,251,423 B2
(45) Date of Patent: Mar. 18, 2025

(54) METHOD OF EFFECTING NEUROPROTECTION USING SOLUBLE NEUREGULIN ISOFORMS

(71) Applicant: Mind-NRG Sàrl, Geneva (CH)

(72) Inventor: André Schrattenholz, Mainz (DE)

(73) Assignee: Mind-NRG Sàrl, Geneva (CH)

( * ) Notice: Subject to any disclaimer, the term of this patent is extended or adjusted under 35 U.S.C. 154(b) by 1071 days.

(21) Appl. No.: 17/012,159

(22) Filed: Sep. 4, 2020

(65) Prior Publication Data

US 2021/0077579 A1   Mar. 18, 2021

Related U.S. Application Data

(60) Continuation of application No. 16/420,755, filed on May 23, 2019, now Pat. No. 10,813,978, which is a division of application No. 15/333,959, filed on Oct. 25, 2016, now Pat. No. 10,350,269, which is a continuation of application No. 14/271,617, filed on May 7, 2014, now abandoned, which is a division of application No. 12/742,983, filed as application No. PCT/EP2008/009715 on Nov. 17, 2008, now abandoned.

(60) Provisional application No. 60/988,576, filed on Nov. 16, 2007.

(51) Int. Cl.
*A61P 25/18* (2006.01)
*A61K 31/5513* (2006.01)
*A61K 38/18* (2006.01)
*A61K 45/06* (2006.01)
*A61P 25/00* (2006.01)
*C07K 14/475* (2006.01)
*C07K 14/485* (2006.01)

(52) U.S. Cl.
CPC ...... *A61K 38/1883* (2013.01); *A61K 31/5513* (2013.01); *A61K 38/1808* (2013.01); *A61K 38/185* (2013.01); *A61K 45/06* (2013.01); *C07K 14/4756* (2013.01); *C07K 14/485* (2013.01)

(58) Field of Classification Search
None
See application file for complete search history.

(56) References Cited

U.S. PATENT DOCUMENTS

| | | | |
|---|---|---|---|
| 5,530,109 A | 6/1996 | Goodearl et al. | |
| 5,763,213 A | 6/1998 | Ho et al. | |
| 5,854,220 A | 12/1998 | Goodearl et al. | |
| 6,087,323 A * | 7/2000 | Gwynne | C07K 14/82 514/8.4 |
| 6,147,190 A | 11/2000 | Goodearl et al. | |
| 7,538,197 B2 | 5/2009 | Schrattenholz | |
| 7,763,591 B2 | 7/2010 | Morishita | |
| 7,919,582 B2 | 4/2011 | Schrattenholz | |
| 10,350,269 B2 | 7/2019 | Schrattenholz | |
| 10,813,978 B2 | 10/2020 | Schrattenholz | |
| 2002/0045577 A1 | 4/2002 | Stefansson et al. | |
| 2004/0180840 A1 | 9/2004 | Ekwuribe et al. | |
| 2004/0191818 A1 | 9/2004 | O'Toole et al. | |
| 2007/0213264 A1 * | 9/2007 | Zhou | C07K 14/4756 435/7.1 |
| 2010/0256066 A1 | 10/2010 | Schrattenholz | |
| 2014/0243269 A1 | 8/2014 | Schrattenholz | |
| 2014/0243270 A1 | 8/2014 | Schrattenholz | |
| 2014/0323408 A1 | 10/2014 | Schrattenholz | |
| 2015/0239948 A1 | 8/2015 | Schrattenholz | |
| 2017/0035849 A1 | 2/2017 | Schrattenholz | |
| 2019/0307848 A1 | 10/2019 | Schrattenholz | |
| 2021/0128687 A1 | 5/2021 | Schrattenholz | |

FOREIGN PATENT DOCUMENTS

| | | | | |
|---|---|---|---|---|
| CA | 2399452 A1 | 8/2001 | | |
| EP | 1252168 A1 | 10/2002 | | |
| EP | 1252186 A2 | 10/2002 | | |
| JP | H10509717 A | 9/1998 | | |
| WO | WO 1992/020798 | 11/1992 | | |
| WO | WO 1996/015812 | 5/1996 | | |
| WO | WO 1996/30403 | 10/1996 | | |
| WO | WO 1999/018976 | 4/1999 | | |
| WO | WO 2001/057051 | 8/2001 | | |
| WO | WO 2001/058948 | 8/2001 | | |
| WO | WO 2003/014156 | 2/2003 | | |
| WO | WO-03014156 A2 * | 2/2003 | ......... | C07K 14/4756 |
| WO | WO 2006/008118 | 1/2006 | | |
| WO | WO 2006/008119 | 1/2006 | | |
| WO | WO 2007/062594 | 6/2007 | | |
| WO | WO 2007/076701 | 7/2007 | | |
| WO | WO 2007/113361 | 10/2007 | | |
| WO | WO 2007/113366 | 10/2007 | | |
| WO | WO 2009/062750 | 5/2009 | | |

OTHER PUBLICATIONS

Pontieri et al (PNAS 92: 12304-12308, 1995).*
Porrino LJ (Psychopharmacology 112: 343-351, 1993).*
Rushe et al (Schizophrenia Res 35: 85-96, 1999).*
Falls (Exp Cell Res 284: 14-30, 2003).*
Kastin et al (J Neurochem 88: 965-970, 2004).*
Schillo et al (J Proteome Res 4: 900-908, 2005).*
Marchionni et al (Cold Spring Harb Symp Quant Biol 61: 459-472, 1996).*
Archer et al., "Effects Of Acute Administration Of Da Agonists On Locomotor Activity: Mptp Versus Neonatal Intracerebroventricular 6-0hda Treatment", Neurotox Res., 2003; 5(1-2), pp. 95-110 (Abstract).
Arnold et al., "Neurodevelopment, Neuroplasticity, And New Genes For Schizophrenia," Prog Brain Res 147:319-345, 2005.

(Continued)

*Primary Examiner* — Kimberly Ballard
*Assistant Examiner* — Aditi Dutt
(74) *Attorney, Agent, or Firm* — COOLEY LLP

(57) ABSTRACT

The present invention refers to soluble Neuregulin-1 isoforms representing Posttranslational Neuregulin-1 modifications as medication in cognition-related neurological disorders, in particular schizophrenia, Alzheimer's and Parkinson's diseases.

11 Claims, 11 Drawing Sheets

(56) References Cited

OTHER PUBLICATIONS

Aviles-Olmos et al., "Exenatide And The Treatment Of Patients With Parkinson's Disease," The Journal Of Clinical Investigation, 123(6), pp. 2730-2736 (2013).
Bao J. et al., (2004) Activity-Dependent Transcription Regulation Of Psd-95 By Neuregulin-1 And Eos., Nat. Neurosci 7:1250-1258 (2004).
Ben-Baruch et al., "Neu Differentiation Factors: a Family of Alternatively Spliced Neuronal and Mesenchymal Factors (43746)", P.S.E.B.M., vol. 206, pp. 221-227, 1994.
Benzel et al., "Interactions Among Genes In The Erbb-Neuregulin Signalling Network Are Associated With Increased Susceptibility To Schizophrenia," Behav Brain Funct 3:31 (2007).
Bertram et al., "Immunohistochemical Evidence For Impaired Neuregulin-1 Signaling In The Prefrontal Cortex In Schizophrenia And In Unipolar Depression," Ann N Y Acad Sci 1096:147-156 (2007).
Blackwood et al., "Are Some Genetic Risk Factors Common To Schizophrenia, Bipolar Disorder And Depression?Evidence From DISC1, GRIK4 And NRG1," Neurotox Res 11:73-83 (2007).
Boissier et al., (1966) [On The Potentiation Of Dopa Effects By Monoamine Oxidase Inhibitors], Psychopharmacologia 8:428-436.
Bordi et al., "Effects of the Metabotropic Glutamate Receptor Antagonist MCPG On Spatial and Context-Specific Learning," 1996, Neuropharmacology 35: 1557-1565.
Britsch, "The Neuregulin-1/Erbb Signaling System In Development And Disease," Adv Anat Embryol Cell Biol 190:1-65 (2007).
Buonanno et al., "Neuregulin And Erbb Receptor Signaling Pathways In The Nervous System," Curr Opin Neurobiol 11:287-296 (2001).
Buresova et al., "On-Demand Platform Improves Accuracy Of The Morris Water Maze Procedure," J Neurosci Methods 15:63-72 (1985).
Burgess et al., "Biosynthetic Processing Of Neu Differentiation Factor. Glycosylation trafficking, and regulated cleavage from the cell surface," Journal Of Biological Chemistry, vol. 270, No. 32, Issue Of Aug. 11, p. 19188-19196, 1995.
Cabantchik et al., "Iron Chelation For Diseases Of Regional Siderosis", Blood, (2013) vol. 122, No. 21, p. 3435.
Cannella B. et al., "The neuregulin, glial growth factor 2, diminishes autoimmune demyelination and enhances remyelination in chronic relapsing model for multiple sclerosis" Proc. Natl. Acad. Sci. USA, 1998, vol. 95, p. 10100-10105.
Carlsson et al., "Systemic Administration Of Neuregulin-1 beta1 Protects Dopaminergic Neurons In A Mouse Model Of Parkinson's Disease," 2011, Journal Of Neurochemistry 117: 1066-1074.
Caudle et al., "Glutamate, Excitotoxicity, And Programmed Cell Death In Parkinson Disease," 2009, Exp Neural., 220 (2), p. 230-3.
Chew et al., "Regulation Of Ion Channel Expression In Neural Cells By Hormones And Growth Factors", Molecular Neurobiology, vol. 18, 1998, p. 175-225.
ClinicalTrials.gov Identifier: NCT00943748, Efficacy and Safety of the Iron Chelator Deferiprone in Parkinson's Disease (FAIR-PARK-I), Jul. 20, 2009.
Costall et al., "Modulation Of Amphetamine Hyperactivity By Dpi Injected Into Rat Nucleus Accumbens [Proceedings]," Br J Pharmacol (1978) 64:461P.
Damulin, "Pathogenic, Diagnostic And Therapeutic Aspects Of Vascular Cognitive Impairment," Consilium Medicum vol. 8, No. 8, 2006.
Dauer and Przedborski, "Parkinson's Disease: Mechanisms And Models," 2003, Neuron vol. 39, 889-909.
Davis et al., "Chronic Parkinsonism Secondary To Intravenous Injection Of Meperidine Analogues," Psychiatry Research 1979;1(3):249-54.
Devos et al., "Targeting Chelatable Iron As A Therapeutic Modality In Parkinson's Disease,"Antioxid Redox Signal, Jul. 10, 2014;21(2):195-210.
Eberhardt et al., "Toxin Models Of Parkinsonism", Eurekah Report, Landes Biosciences, 2007, pp. 153-173.
Eilam et al., "Activity-Dependent Regulation Of Neu Differentiation Factor/Neuregulin Expression In Rat Brain," Proceedings Of The National Academy Of Sciences Of The USA vol. 95, Feb. 1998 (Feb. 1998), pp. 1888-1893, Xp002187768; Abstract; p. 1890; Figure 2, p. 1889; Figure 1; p. 1892; Figure 5.
Esper et al., (2006) "Neuregulins: Versatile Growth And Differentiation Factors In Nervous System Development And Human Disease," Brain Res Rev 51:161-175.
Esposito et al., "Non-Steroidal Anti-Inflammatory Drugs In Parkinson's Disease," Jun. 2007, Experimental Neurology 205(20):295-312.
Fallon et al., "Constitutive Activation Of The Neuregulin-1/Erbb Signaling Pathway Promotes The Proliferation Of A Human Peripheral Neuroepithelioma Cell Line", 2004, Journal Of Neuro-Oncology 66: 273-284.
Falls, "Neuregulins: Functions, Forms, And Signaling Strategies," 2003, Experimental Cell Research 284:14-30.
Falquet et al., "The Prosite Database, Its Status In 2002," Nucleic Acids Res (2002) 30:235-238.
Farmer et al., "The Genetics Of Bipolar Affective Disorder," Curr Opin Psychiatry (2007) 20:8-12.
Fazzini et al., "GM1 Gangliosides Alter Acute MPTP-Induced Behavioural And Neurochemical Toxicity In Mice," Journal Of The Neurological Sciences, vol. 99 (1), (1990), 59-68 (Abstract).
Feigin et al., "Recent advances in Huntington's disease: implications for experimental therapeutics," 2002, Curr. Opin. Neurol. 15(4): 483-489.
Final rejection issued by the United States Patent and Trademark Office for U.S. Appl. No. 12/742,983, filed Sep. 24, 2012, 13 pages.
Final rejection issued by the United States Patent and Trademark Office for U.S. Appl. No. 12/742,983, filed Jun. 9, 2014, 16 pages.
Fischbach, "NRG1 And Synaptic Function In The CNS," Neuron (2007), 54:495-497.
Genbank Aaa58639.1, "Heregulin-Beta1 [*Homo sapiens*]." Apr. 27, 1993. Two pages in total.
Gerlach et al., "Animal models of Parkinson's disease: an empirical comparison with the phenomenology of the disease in man", J Neural Transm, 1996, 103(8-9) pp. 987-1041 (Abstract).
Geuna et al., (2007), "Nerve Regeneration Along Bioengineered Scaffolds," Microsurgery 27:429-438.
Gilert and Machluf, "Nano To Micro Delivery Systems: Targeting Angiogenesis In Brain Tumors," Journal Of Angiogenesis Research 2:20 (2010), 1 Page.
Glabe, "Biomedicine. Avoiding Collateral Damage In Alzheimer's Disease Treatment," Science (2006), 314:602-603.
Go et al., "Neuregulin-1 Polymorphism In Late Onset Alzheimer's Disease Families With Psychoses," Am J Med Genet B Neuropsychiatr Genet. (2005), 139:28-32.
Golub et al., "Behavioral Characteristics Of A Nervous System-Specific Erbb4 Knock-Out Mouse," Behav Brain Res (2004), 153:159-170.
Graus et al., "Antibodies And Neuronal Autoimmune Disorders Of The CNS", J. Neurol., Apr. 2010;257(4):509-17.
Gresham-Smith et al., Oxford Handbook Of Clinical Pharmacology And Pharmacotherapy, Moscow, "Meditsina", 2000, p. 136-137.
Guo et al., "Neuroprotective Effects Of Neuregulin-1 In Rat Models Of Focal Cerebral Ischemia," Brain Res (2006), 1087:180-185.
Haddaad and Sharma, "Adverse Effects Of Atypical Antipsychotics: Differential Risk And Clinical Implications," CNS Drugs (2007), 21:911-936.
Hahn et al., "Altered Neuregulin 1-Erbb4 Signaling Contributes To Nmda Receptor Hypofunction In Schizophrenia," Nat Med 12:824-828 (2006).
Halliday et al., "Alzheimer's disease and inflammation: a review of cellular and therapeutic mechanisms", Clin Exp Pharmacol Physiol 27(1-2): 1-8, 2000.
Hanninen et al., "Interleukin-1 Beta Gene Polymorphism And Its Interactions With Neuregulin-1 Gene Polymorphism Are Associated With Schizophrenia," Eur Arch Psychiatry Clin Neurosci Feb. 2008; 258(1)10-5. Epub Sep. 27, 2007.

(56) References Cited

OTHER PUBLICATIONS

Ho et al., "Sensory And Motor Neuron-Derived Factor". The Journal Of Biological Chemistry. vol. 270. No. 24, Issue Of Jun. 16, p. 14523-14532, 1996.
Hoglinger et al., "The pRb/E2F Cell-Cycle Pathway Mediates Cell Death In Parkinson's Disease," Proc Natl Acad Sci USA 104:3585-3590 (2007).
Hoglinger et al., "Dopamine Depletion Impairs Precursor Cell Proliferation In Parkinson Disease," Nat Neurosci 7:726-735 (2004).
Holbro, T. and Hynes "ErbB Receptors: Directing Key Signaling Networks Throughout Life," Annu Rev Pharmacol Toxicol (2004), 44:195-217.
Hong, "Evidence Of Missense Mutations On The Neuregulin 1 Gene Affecting Function Of Prepulse Inhibition," Biol Psychiatry, Jan. 1, 2008; 63(1): 17-23. Doi:10.1016/j.biopschy.2007.05.011.
Hu et al., "Bace1 Modulates Myelination In The Central And Peripheral Nervous System," Nat Neurosci (2006) 9:1520-1525.
Hutter et al., "BL-1023 Improves Behavior And Neuronal Survival In 1-Methyl-4-Phenyl-1,2,3,6-Tetrahydropyridine-Intoxicated Mice", Neuroscience, (2011), 180:293-304.
Imamachi et al., "The Non-NMDA Glutamate Receptor Antagonist CNQX Augments Lidocaine Antinociception Through A Spinal Action In Rats," Anesth Analg; 1999, 89:416-21.
International Preliminary Report on Patentability and Written Opinion issued by the International Searching Authority for Application No. PCT/EP2008/009715, dated May 18, 2010, 7 pages.
International Search Report issued by the International Searching Authority for Application No. PCT/EP2008/009715, dated Jul. 29, 2009, 4 pages.
Jane et al., "Stereospecific Antagonism By (+)-a-Methyl-4-Carboxyphenylglycine (MCPG) of (1S, 3R)-ACPD-Induced Effects In Neonatal Rat Motoneurones And Rat Thalamic Neurones", Neuropharmacology 1993, 32:725.
Joyce et al., "Low Dose Pramipexole Is Neuroprotective In The Mptp Mouse Model Of Parkinson's Disease, And Downregulates The Dopamine Transporter Via The D3 Receptor", BMC Biology, 2004, 2:22, pp. 1-12.
Kani et al., "The Extracellular Domains Of ErbB3 Retain High Ligand Binding Affinity At Endosome pH And In The Locked Conformation", Biochemistry, 2005, 44:15842-15857.
Karoutzou et al. "The Myelin-Pathogenesis Puzzle In Schizophrenia: A Literature Review," Mol Psychiatry 13:245-260 (2008).
Kastin et al., "Neuregulin-1-β1 enters Brain and Spinal Cord by Receptor-mediated transport" Journal of Neurochemistry, 2004, 88: 965-970.
Kim et al., "Exendin-4 protects dopaminergic neurons by inhibition of microglial activation and matrix metalloproteinase-3 expression in an animal model of Parkinson's disease," Journal of Endocrinology (2009), 202, 431-439.
Kwon et al., "Neuregulin-1 Reverses Long-Term Potentiation At CA1 Hippocampal Synapses," J Neurosci (2005), 25:9378-9383.
Langston et al., "Evidence Of Active Nerve Cell Degeneration In The Substantia Nigra Of Humans Years After 1-Methyl-4-Phenyl-1,2,3,6-Tetrahydropyridine Exposure", Ann Neurol. Oct. 1999; 46(4):598-605.
Langston et al., "MPTP-Induced Parkinsonism In Human And Non-Human Primates—Clinical And Experimental Aspects." Acta Neurol Scand Suppl. 1984;100:49-54 (Abstract).
Li et al., "ErbB4, a receptor of the schizophrenia-linked protein neuregulin-1, controls glutamatergic synapse maturation and plasticity," Neuron 54:583-597 (2007).
Liberatore et al., "Inducible Nitric Oxide Synthase Stimulates Dopaminergic Neurodegeneration In The MPTP Model Of Parkinson Disease," Nat Med 5:1403-1409 (1999).
Lu et al., "Post-Translational Processing Of Membrane-Associated Neu Differentiation Factor Proisoforms Expressed In Mammalian Cells," The Journal Of Biological Chemistry, vol. 270, No. 9, Issue Of March 3, pp. 4775-4783, 1995.

Lu et al., "Studies On The Structure And Function Of Glycosylated And Nonglycosylated Neu Differentiation Factors", The Journal Of Biological Chemistry, vol. 270, No. 9, Issue Of March 3, p. 4784-4791, 1995.
Mahajan et al., "Immunological Assays For Chemokine Detective In In-Vitro Culture Of CNS Cells," 2003, Biol Proced Online 5(1): 90-102.
Malenka and Nicoll, "Long-Term Potentiation—A Decade Of Progress?," Science 1999, 285: 1870-1874.
Marchionni et al., "Neuregulins As Potential Drugs For Neurological Disorders," 1996, Cold Spring Harbor Symposia On Quantitative Biology, vol. Lxi, Cold Spring Harbor Laboratory Press, 61:459-472.
Matthew et al., "Alpha7 Nicotinic Acetylcholine Receptor mRNA Expression And Binding InPostmortem Human Brain Are Associated With Genetic Variation In Neuregulin 1," Hum Mol Genet. 16(23):2921-2932 (2007).
Mcintosh et al., "The Effects Of A Neuregulin 1 Variant On White Matter Density And Integrity," Mol Psychiatry Nov. 2008; 13(11):1054-1059. Epub Oct. 9, 2007.
Meeks et al., "The Neurobiology Of Neuropsychiatric Syndromes In Dementia," Curr Opin Psychiatry (2006), 19:581-586.
Meyer-Luehmann et al., "Exogenous Induction Of Cerebral Beta-Amyloidogenesis Is Governed By Agent And Host," Science 313:1781-1784 (2006).
Meyer et al., "Isoform-specific expression and function of neuregulin," Development, vol. 124, pp. 3575-3586, 1997.
Mirapex. Label Information. Aug. 2012, 20 Pgs.
Morris, "Synaptic Plasticity And Learning: Selective Impairment Of Learning In Rats And Blockade Of Long-Term Potention In Vivo By The N-Methyl-D-Aspartate Receptor Antagonist AP5," Journal Of Neuroscience, 1989, 9(9):3040-57.
Muller and Schwarz, "Schizophrenia As An Inflammation-Mediated Dysbalance Of Glutamatergic Neurotransmission," Neurotox Res (2006), 10:131-148.
Muraulirishnan and Mohanakumar, "Neuroprotection By Bromocriptine Against 1-Methyl-4-Phenyl-1,2,3,6-Tetrahydropyridine-Induced Neurotoxicity In Mice," FASEB Journal (1998) Jul. 12(10):905-912.
Nadri et al., (2007), "Oxygen Restriction Of Neonate Rats Elevates Neuregulin-1alpha Isoform Levels: Possible Relationship To Schizophrenia," Neurochem Int 51:447-450.
Niceprot View Of Swiss-Prot: Q15491, Oct. 9, 2004.
Odin et al., "Efficacy And Safety Of High-Dose Cabergoline In Parkinson's Disease", Acta Neurol Scand, (2006), 113 (1) pp. 18-24 (Abstract).
Office Action in U.S. Appl. No. 11/991,219, filed Dec. 14, 2012, 17 pgs.
Office Action in U.S. Appl. No. 12/742,983, filed Mar. 23, 2012, 13 pgs.
Office Action in U.S. Appl. No. 12/742,983, filed Sep. 20, 2013, 8 pgs.
Owen et al., "The Genetic Deconstruction Of Psychosis," Schizophr Bull (2007), 33:905-911.
Okazi et al., "Neuregulin-B Induces Expression Of An Nmda-Receptor Subunit," Nature, vol. 390, Dec. 18/25, 1997, pp. 691-694.
Ozaki M, Itoh K, Miyakawa Y, Kishida H, Hashikawa T (2004) "Protein Processing And Releases Of Neuregulin-1 Are Regulated In An Activity-Dependent Manner," J Neurochem 91:176-188.
Parlodel, Label Information, Updated Jan. 2012, 17 Pgs.
Pertusa et al., "Transciptional Control Of Cholesterol Biosynthesis In Schwann Cells By Axonal Neuregulin 1," J Biol Chem Sep. 28, 2007;282(39):28768-78.
Phillips, "The Challenge Of Gene Therapy And DNA Delivery," J Pharm Pharmacol 2001, 53: 1169-1174.
Press Release, Boehringer Ingelheim "Once-Daily Mirapex Er Now Approved By Fda For Both Early And Advanced Parkinson's Disease", Mar. 2010, 4 Pgs.
Przedborski and Vila,(2003), "The 1-Methyl-4-Phenyl-1,2,3,6-Tetrahydropyridine Mouse Model: A Tool To Explore The Pathogenesis Of Parkinson's Disease," Ann N Y Acad Sci 991:189-198.
Raabe et al., "Localization of neuregulin isoforms and erbB receptors in myelinating glial cells," Glia, vol. 45, pp. 197-207, 2004.

(56) References Cited

OTHER PUBLICATIONS

R & D Systems, "Recombinant Human Nrg1-B1/Hrg1-B1 Extracellular Domain, Catalog No. 377-Hb/Cf," www.Rndsystems.Com. Apr. 27, 1993, 1 page.
Radde et al., "Abeta42-Driven Cerebral Amyloidosis In Transgenic Mice Reveals Early And Robust Pathology," Embo Rep 7:940-946 (2006).
Rimer,"Neuregulin-1 Immunoglobulin-Like Domain Mutant Mice: Clozapine Sensitivity And Impaired Latent Inhibition," Neuroreport 16:271-275 (2005).
Ross et al., "Neurobiology Of Schizophrenia," Neuron (2006), 52:139-153.
Schillo et al., "Integrative Proteomics: Functional And Molecular Characterization Of A Particular Glutamate-Related Neuregulin Isoform," J Proteome Res 4: 900-908, 2005.
Schrattenholz and Soskic, "NMDA Receptors Are Not Alone: Dynamic Regulation Of NMDA Receptor Structure And Function By Neuregulins And Transient Cholesterol-Rich Membrane Domains Leads To Disease-Specific Nuances Of Glutamate-Signalling," Curr Top Med Chem 6:663-686 (2006).
Schmidt and Ferger, "Neurochemical Findings In The Mptp Model Of Parkinson's Disease," Journal Of Neural Transmission, (2001), 108 (11):1263-82. (Abstract).
Schneider et al., "A Randomized, Controlled, Delayed Start Trial Of GM1 Ganglioside In Treated Parkinson's Disease Patients", J. Neurol Sci, (2013), 324(1-2), pp. 140-148.
Schubert, "Alzheimer Disease: Bace1 Branches Out," Nat Med (2006), 12:1123.
Scolnick et al., "Schizophrenia: Do The Genetics And Neurobiology Of Neuregulin Provide A Pathogenesis Model?," Harv Rev Psychiatry (2006), 14:64-77.
Sekiyama et al., "Structure-Activity Relationships Of New Agonists And Antagonists Of Different Metabotropic Glutamate Receptor Subtypes," Br. J. Pharmacol. 1996, 117:1493-1503.
Sheldon and Robinson, "The Role Of Glutamate Transporters In Neurodegenerative Diseases And Potential Opportunities For Intervention," Neurochem Int., 51 (6-7), pp. 333-355 (2007).
Shyu et al., "Neuregulin-1 Reduces Ischemia-Induced Brain Damage in Rats", 2004, Neurobiology of Aging, 25(7), pp. 935-944.
Sinemet, Label Information, Updated Jan. 2011, 13 pgs.
Steece-Collier et al,. "Etiology of Parkinson's disease: genetics and environment revisited", Proc Natil Acad Sci USA 15 (4): 483-489, 2002.
Stefansson, H. et al., "Neuregulin 1 and susceptibility to schizophrenia" Am. J. Hum. Genet., 2002, vol. 71, p. 877-892.
Summary of Product Characteristics (European Commission), Symmetrel Capsules, Feb. 19, 2014, 5 pgs.
Swiss-Prot: Q15491, Oct. 9, 2004.
Symmetrel, Label Information, Jan. 2009, 15 pgs.
Tatton et al., "Rescue of dying neurons: a new action for deprenyl in MPTP parkinsonism", J. Neurosci Res., Dec. 1991., 30(4), pp. 666-672 (Abstract).
Teismenn et al., "Inhibition of the cyclooxygenase isoenzymes COX-1 and COX-2 provide neuroprotection in the MPTP-mouse model of Parkinson's disease," SYNAPSE 2001, 39:167-174.
Thomson et al., "Association Of Neuregulin 1 With Schizophrenia And Bipolar Disorder In A Second Cohort From The Scottish Population," Mol Psychiatry 12:94-104 (2007).
Vidal et al., "Making Sense Of Antisense," Eur J Cancer 2005, 41: 2812-2818.
Vila and Przedborski, "Targeting Programmed Cell Death In Neurodegenerative Diseases," Nat Rev Neurosci (2003), 4:365-375.
Wang et al., "Contrasting Effects Of Mitogenic Growth Factors On Myelination In Neuron-Oligodendrocyte Co-Cultures," Glia 2007, 55:537-545.
Warren et al., "The N-Terminal Domains Of Neuregulin 1 Confer Signal Attenuation," Journal Of Biological Chemistry Sep. 15, 2006, 281(37):27306-27316.

Watkins and Collingridge, "Phenylglycine Derivatives As Antagonists Of Metabotropic Glutamate Receptors", 1994, Trends Pharmacol. Sci.(vol. 15), pp. 333-342.
Wen et al., "Structural And Functional Aspects Of The Multiplicity Of Neu Differentiation Factors," Molecular And Cellular Biology, vol. 14, No. 3, Mar. 1994 (Mar. 1994), pp. 1909-1919, Xp002064746; Issn: 0270-7306; Abstract; p. 1912; Figure 1.
Wikipedia Article "Cnqx," May 20, 2009.
Wikipedia Article "Nifedipine", Jan. 10, 2010.
Wikipedia article "AP-5", Dec. 18, 2009.
Willem et al., "Control Of Peripheral Nerve Myelination By The Beta-Secretase BACE1," Science (2006) 314:664-666.
Wolpowitz et al., "Cysteine-Rich Domain Isoforms For The Neuregulin-1 Gene Are Required For Maintenance Of Peripheral Synapses," Neuron 25(1):79-91, 2000.
Woo et al., "Neuregulin-1 Enhances Depolarization-Induced Gaba Release," Neuron (2007), 54:599-610.
Xie et al., "Association of PSD-95 with ErbB4 facilitates neuregulin signaling in cerebellar granule neurons in culture," Journal of Neurochemistry 100:62-72 (2007).
Xu et al., "Neuroprotection By Neuregulin-1 Following Focal Stroke Is Associated With The Attenuation Of Ischemia-Induced Pro-Inflammatory And Stress Gene Expression," Neurobiol Dis 19:461-470 (2005).
Xu et al., "Neuregulin-1 Is Neuroprotective And Attenuates Inflammatory Responses Induced By Ischemic Stroke," Biochem Biophys Res Commun (2004), 322:440-446.
Xu Z. et al., "Extended therapeutic window and functional recovery after intraarterial administration of neuregulin-1 after focal ischemic stroke" Journal of Cerebral Blood Flow & Metabolism, 2006, vol. 26, p. 527-535.
Yang et al., "Neuregulin-Induced Expression of the Acetylcholine Receptor Requires Endocytosis of Erbb Receptors," Mol Cell Neurosci (2005), 28:335-346.
Yurek, D. M. et al., "Supranigral injection of neuregulin 1-β induces striatal dopamine overflow" Brain Research, 2004, vol. 1028, p. 116-119.
Zelapar, Label Information, Feb. 2008, 19 Pgs.
Zelapar, Label Information, updated Aug. 2014, 14 pages.
Zhang L. et al., "Neurotrophic and neuroprotective effects of the neuregulin glial growth factor-2 on dopaminergic neurons in rat primary midbrain cultures," Journal of Neurochemistry, 2004, vol. 91, p. 1358-1368.
Zhao et al., "Neuregulins Promote Survival and Growth of Cardiac Myocytes," The Journal Of Biological Chemistry, 1998, vol. 273, No. 17, p. 10261-10269.
Banks, A., "Characteristics of compounds that cross the blood-brain barrier," BMC Neurol. Jun. 12, 2009;9 Suppl 1(Suppl 1):S3, 5 pages.
Castillo et al., "Neuregulin-1 isoform induces mitogenesis, KCa and Ca2+ currents in PC12 cells. A comparison with sciatic nerve conditioned medium," Brain Research (2006) 1110:64-75.
Pankonin et al., "Specific Structural Features of Heparan Sulfate Proteoglycans Potentiate Neuregulin-1 Signaling," The Journal of Biological Chemistry, Jan. 2005, vol. 280, No. 1, pp. 383-388.
Rösler et al., "Biodistribution and brain permeability of the extracellular domain of neuregulin-1-β1," Neuropharmacology (2011) 61:1413-1418.
[Author Unknown] "Neuregulin 1" Wikipedia [online] https://en.wikipedia.org/w/index.php?title=Neuregulin_1&oldid=1215826496 (Access Date: Sep. 12, 2024); 18 pages.
Buckel, P., "Recombinant Proteins for Therapy", Tips (Dec. 1996); 17: 450-456.
Stopford, C. L., et al., "Distinct Memory Profiles in Alzheimer's Disease", Cortex (Oct. 2007); 43: 846-857.
[Author Unknown, Date Unknown] "Parkinson's Disease Models", Neuro Detective International; 4 pages.
Emborg, M. E., "Evaluation of animal models of Parkinson's disease for neuroprotective strategies", Journal of Neuroscience Methods (2004); 139(2): 121-143.
Gündüz, B., et al., "The effects of leptin hormone on locomotor activity in Syrian hamsters (*Mesocricetus auratus*)", Turkish Journal of Biology (2011); 35(6): 727-734.

(56) References Cited

OTHER PUBLICATIONS

Lang, A. E., et al., "Randomized controlled trial of intraputamenal glial cell line-derived neurotrophic factor infusion in Parkinson disease", Annals of Neurology (2006); 59(3): 459-466.

Noel, N., et al., "Preclinical Characterization of MIN-301, a Neuregulin-1 Fragment, as a Potential Disease-Modifying Therapy for Parkinson's Disease", Poster, Minerva Neurosciences Inc., ACNP Meeting (Dec. 6-10, 2015); 1 page.

Rosenegger, D., et al., "A quantitative proteomic analysis of long-term memory", Molecular Brain (2010); 3: 1-10.

Sheikov, N., et al., "Effect of focused ultrasound applied with an ultrasound contrast agent on the tight junctional integrity of the brain microvascular endothelium", Ultrasound in Medicine & Biology (2008); 34(7): 1093-1104.

U.S. Appl. No. 12/742,983, Exhibit A: U.S. Appl. No. 10/495,132: Declaration of Dr. Akiko Ishida, signed Oct. 5, 2007; 9 pages.

U.S. Appl. No. 12/742,983: Declaration of Prof. Andre Schrattenholz, signed Jul. 21, 2012; 11 pages.

U.S. Appl. No. 12/742,983: Declaration of Prof. Andre Schrattenholz, signed Mar. 20, 2013; 8 pages.

U.S. Appl. No. 15/333,959: Declaration of Amos Korczyn, signed Apr. 26, 2017, with Appendix 1; 146 pages.

U.S. Appl. No. 16/420,755: Declaration of Remy Luthringer, signed Apr. 16, 2020, with Exhibit B and C; 21 pages.

\* cited by examiner

METHOD OF EFFECTING NEUROPROTECTION USING SOLUBLE NEUREGULIN ISOFORMS

CROSS REFERENCE TO RELATED APPLICATION

This application is a continuation of U.S. patent application Ser. No. 16/420,755, now allowed, filed May 23, 2019, which is a division of U.S. patent application Ser. No. 15/333,959, filed Oct. 25, 2016, now U.S. Pat. No. 10,350,269, which is a continuation of U.S. patent application Ser. No. 14/271,617, filed May 7, 2014, which is a division of U.S. patent application Ser. No. 12/742,983, filed May 14, 2010, which is a 35 U.S.C. 371 National Phase Entry Application from PCT/EP2008/009715, filed Nov. 17, 2008, which claims priority from and the benefit of U.S. Ser. No. 60/988,576 filed on Nov. 16, 2007, each of which are incorporated herein in their entireties by reference.

DESCRIPTION

The present invention refers to Neuregulin-1 isoforms soluble in physiological solutions representing posttranslational Neuregulin-1 modifications or splice variants as medication in cognition-related neurological disorders, in particular schizophrenia, Alzheimer's and Parkinson's diseases.

BACKGROUND OF THE INVENTION

Neuregulins (NRG) have emerged as key regulators of synaptic signalling. These transmembrane proteins are encoded by four genes (NRG-1, -2, -3 and -4), and their diversity is further increased by alternate RNA splicing and promoter usage and in particular by posttranslational modifications like proteolytic processing which leads to release of soluble isoforms from membrane-bound holoproteins. Moreover there is evidence of phosphorylation and glycosylation (Buonanno and Fischbach 2001). They are characterized by different extracellular domains and are ligands of ErbB receptor tyrosine kinases, which have downstream connotations to neuroinflammation and gene transcription (Holbro and Hynes 2004). In particular, soluble isoforms of NRG-1 are produced from the transmembrane form of NRG through proteolytic cleavage during electrical stimulation and subsequently secreted as activity-dependent synaptic modulators (Ozaki et al. 2004).

A truncated isoform of NRG-1, presumably (31, comprising the N-terminal extracellular domain (ECD) of the entire membrane protein, which has been found to be correlated to learning and memory (Schillo et al. 2005a; WO03/014156). Functional studies have demonstrated, that NRG-1 directly regulates NMDA receptor subunit composition (Ozaki et al. 1997; Eilam et al. 1998). Moreover it has been shown that NRG-1 fragments of this type have neuroprotective properties in vivo by antiapoptotic effects (Xu et al. 2005A; Xu et al. 2005B; Xu et al. 2004).

Very recently it became clear that NRG-1 has a central role in human neurological diseases due to NRG-dependent regulation of NMDA receptors (Schrattenholz and Soskic 2006), and subsequent downstream events like excitotoxicity, neuroinflammation and apoptosis (see FIG. 1 for summary). There are results showing that NRG 1 plays a pivotal role in conditions ranging from amyotrophic lateral sclerosis, Alzheimer's and Parkinson' disease, to stroke and schizophrenia (Britsch 2007).

This fundamental significance of NRG-1 implies that next to neuroprotection and a positive role in cognition-related learning and memory, NRG-1 represents a crucial neurotrophic factor in regeneration of neuronal tissue after a variety of lesions, in a variety of specific brain regions and cell types. Obviously it is the crucial factor for maintenance and repair of the integrity of neuronal circuitry: neuroprotective and with roles in correct regeneration after loss of function, as well as in the formation of activity-dependent neuronal plasticity.

The interest in Neuregulin 1 β was further fueled considerably when Kastin et al., 2004, showed that Neuregulin 1 β is able to cross the blood-brain barrier. That opened the perspective for the therapeutic usage of Neuregulin 1 β.

Latest research proved the breadth of application in neuroprotection. Independently it was shown in two publications that Neuregulin 1 is also a substrate of BACE (β-secretase, β-amyloid converting enzyme), which indicates the relevance of Neuregulin 1 in Alzheimer's disease (Glabe 2006; Schubert 2006).

Further, it was found that in Schwann cells neuregulin-1 increases the transcription of the 3-hydroxy-3-methylglutaryl-Coenzyme-A reductase, the rate-limiting enzyme for cholesterol biosynthesis in Schwann cells (Pertusa et al. 2007). This has far reaching implications for all conditions where the myelin sheath is affected, e.g. schizophrenia and multiple sclerosis, or cognition-related functions, where so-called "cholesterol-rich rafts" are involved (Schrattenholz and Soskic 2006). Schwann cell surrounding axons express NRG1 receptors ErbB2/ErbB3 and soluble NRG1 α and β under physiological conditions Following denervation, adult Schwann cells leave the contact with axon, change their morphology, stop expressing NRG1 β, and upregulate NRG1 α and ErbB2/ErbB3 expression (Geuna et al. 2007; Karoutzou et al. 2007).

In addition, genetic epidemiologic research shows the clear association of Neuregulin 1 to schizophrenia and to Alzheimer disease, and in particular to its psychotic forms (Farmer et al., 2007).

Some recent genetic population analyses show, that certain NRG-1-SNP's are associated with Alzheimer and schizophrenia (Go et al. 2005; Scolnick et al. 2006; Ross et al. 2006; Meeks et al. 2006; Farmer et al. 2007). The implications of these findings are related to other proteins of the functional NRG-containing complex depicted in FIG. 1 (ErbB receptor: (Benzel et al. 2007; Thomson et al. 2007; Hahn et al. 2006). There is also an implication for NRG-1 in multiple sclerosis (Esper et al. 2006).

There are results suggesting that the molecular mechanism of the association between NRG1 risk alleles and schizophrenia may include down-regulation of nicotinic acetylcholine receptors of alpha7subtype (Mathew et al. 2007).

According to the present invention it was found that recombinant soluble Neuregulin-1☐ isoforms show pharmceutical efficacy in animal models for learning and memory, schizophrenia, Alzheimer's disease and Parkinson's disease. After i.v. administration, Neuregulin-1☐ isoforms were active at concentrations which are significantly lower than concentrations of control medicaments.

Thus, a first aspect of the present invention is the use of a recombinant soluble Neuregulin-1 isoform for the manufacture of a medicament for the treatment of neurological conditions, particularly of cognition-related neurological conditions.

A further aspect of the present invention is a pharmaceutical composition or kit comprising (i) a recombinant soluble Neuregulin-1 isoform and (ii) a further medicament particularly for the treatment of neurological conditions, particularly of cognition-related neurological conditions.

Still a further aspect of the present invention is the use of a recombinant soluble Neuregulin-1 isoform for memory and cognition enhancement for the manufacture of a medicament.

Still a further aspect of the present invention is a method of treating a neurological condition comprising administering a recombinant soluble Neuregulin-1 isoform in a pharmaceutically effective amount to a subject in need thereof.

Still a further aspect of the present invention is a method for enhancing memory and cognition comprising administering a recombinant soluble Neuregulin-1 isoform in a pharmaceutically effective amount to a subject in need thereof.

Still a further aspect of the present invention is a co-administration of a recombinant soluble Neuregulin-1 isoform together with a further medicament.

According to the present invention, soluble Neuregulin-1 isoforms have been found to be effective for the treatment of neurological conditions, particularly conditions, such as psychotic disorders like schizophrenia, bipolar disorder and depression, neurodegenerative disorders, like Parkinson's disease, Alzheimer's disease, Multiple Sclerosis (MS), or Amylotrophic Lateral Sclerosis (ALS), epilepsy or neurological injury like stroke, traumatic brain injury and spinal chord injury. Preferred is the treatment of schizophrenia, in particular cognition-related aspects of schizophrenia, Parkinson's disease and Alzheimer's disease. Further, the invention also refers to the use of recombinant soluble Neuregulin-1 isoforms for memory and cognition enhancement, particularly for reducing and/or inhibiting memory and cognition loss associated with a neurological condition such as Alzheimer's disease and schizophrenia.

The recombinant soluble Neuregulin-1 isoform is preferably a human Neuregulin-1 isoform, i.e. a recombinant isoform comprising the primary amino acid sequence of a naturally occurring human Neuregulin-1 isoform or a sequence which has a identity of at least 90%, preferably at least 95% and most preferably of at least 98% based on the total length of the recombinant isoform.

The soluble recombinant Neuregulin-1 isoform of the present invention preferably comprises at least a portion of the extracellular domain of the corresponding Neuregulin-1, e.g. at least a portion of the extracellular domain of a human Neuregulin, e.g. human Neuregulin-1 β.

The recombinant soluble Neuregulin isoform of the present invention preferably has a length of up to 250 amino acids, e.g. 150 to 250 amino acids. The molecular weight of the Neuregulin isoform is preferably of about 15 to about 35 KD, particularly about 25 to about 32 KD, as measured e.g. by SDS-polyacrylamide electrophoresis (PAGE). The recombinant soluble Neuregulin-1 isoform, particularly the recombinant Neuregulin-1 β isoform, has an isoelectric point (pI) of about 4 to about 9.5, preferably of about 4 to about 6. The isoform may be an unmodified polypeptide which consists of an unmodified amino acid sequence or a modified polypeptide, wherein the modification may be selected from phosphorylation, glycosylation, methylation, myristylation, oxidation and any combination thereof. In an especially preferred embodiment, the Neuregulin-1 isoform comprises at least one phosphorylated amino acid residue. Further, the present invention encompasses conjugation to heterologous moieties such as poly(alkyleneoxide) moieties, particularly polyethylene glycol moieties.

The recombinant soluble isoforms may be administered according to any route by which effective delivery into the target tissue, e.g. the nervous system, particulary the central nervous system, such as brain and/or spinal chord, is achieved. It was found that pharmaceutically effective concentrations of Neuregulin isoforms may be achieved by systemic administration. For example, the isoforms may be administered by injection or infusion, e.g. by intravenous injection. The isoforms are preferably administered in an amount of 0.1 to 5000 ng/kg body weight, particularly in an amount of 2 to 1000 ng/kg body weight and more particularly in an amount of 3 to 600 ng/kg body weight of the subject to be treated, depending on the type and severity of the condition to be treated. In other embodiments of the present invention the soluble isoforms may also be administered locally, e.g. by direct administration into the central nervous system, e.g. into the spinal chord and/or into the brain. Also administration at higher dosages of up to 500 µg/kg by i.p. or s.c. injections, or inhalation devices are may be considered. Preferably the subject to be treated is a mammal, more preferably a human patient.

The soluble recombinant Neuregulin-1 isoforms may be administered as a stand-alone medication, i.e. as a monotherapy or as a co-medication, i.e. in combination with a further medicament, particularly with a further medicament which is suitable tor the treatment of a neurological condition. Examples of further medicaments are compounds affecting catecholamine metabolism, acetylcholine esterase inhibitors, MAO-B- or COMT-inhibitors, Memantine-type channel blockers, dopamine or serotonine receptor agonists or antogonists, catecholamine or serotonine reuptake inhibitors or any type of antipsychotic medicaments like clozapine or olanzapine or gabapentin-like drugs, particularly in the treatment of Alzheimer's and Parkinson's diseases, schizophrenia, bipolar disorder, depression or other neurological conditions. Additional examples of further medicaments are neuroprotective agents such as PARP-1 inhibitors, e.g. as disclosed in WO 2006/008118 and WO 2006/008119, which are herein incorporated by reference.

Thus, an embodiment of the present invention refers to the combination of a recombinant soluble Neuregulin-1 isoform as described herein with a medicament for the treatment of psychotic disorders such as schizophrenia, bipolar disorders and depression, e.g. olanzapine or clozapine. A further embodiment refers to the combination of a recombinant soluble Neuregulin-1 isoform and a medicament for the treatment of a neurodegenerative disease such as Parkinson's disease, Alzheimer's disease, MS or ALS. Still a further embodiment refers to the combination of a recombinant soluble Neuregulin-1 isoform and a medicament for the treatment of neurological injury, such as stroke, traumatic brain injury or spinal chord injury.

The combination therapy may be effected by co-administering the recombinant soluble Neuregulin-1 isoform and the further medicament in the form of a pharmaceutical composition or kit, wherein the individual medicaments are administered by separate or common administration.

The Neuregulin-1 isoform may be a Neuregulin-1 Type I, Type II, Type III, Type IV, Type V or Type VI isoform, preferably a Neuregulin-1 β isoform, a Neuregulin-1 α isoform or a Sensory and motor neuron-derived factor (SMDF) isoform, particularly a Neuregulin-1 β isoform and more particularly a human Neuregulin-1 β isoform.

Neuregulin 1 β isoforms are actively transported through the blood brain barrier. The excellent bioavailability of Neuregulin 1 β in the brain after i.v./i.p. Injection, as shown in the Examples paves the way towards a therapeutic application of NRG 1 β.

Its combination of antiapoptotic, myelin-stabilizing, anti-inflammatory properties, together with the direct interaction with BACE opens opportunities in the treatment of stroke, Alzheimer, M S and schizophrenia and other neurological conditions.

As outlined above, the present application encompasses the use of unmodified and modified Neuregulin-1 isoforms, particularly Neuregulin-1 β isoforms. There is evidence that posttranslational modifications like proteolytic processing, phosphorylation and glycosylation take place at certain amino acid residues of the Neuregulin-1, and in particular its extracellular domain. In particular the release of soluble fragments of Neuregulin-1 has been reported (Buonanno and Fischbach 2001; Fischbach 2007). Potential oxidation has been reported as well (Nadri et al. 2007).

The present inventors have obtained evidence that preferred physiologically active Neuregulin-1 β isoforms comprise the extracellular domain of Neuregulin-1 β or a part thereof which has been post-translationally modified. Preferably, the isoforms have been modified by phosphorylation, wherein 1, 2, 3 or more amino acid side chain residues, particularly side chain residues having an OH-group such as Tyr, Ser or Thr, have been phosphorylated. Preferred phosphorylation sites are located at amino acid positions 79-82, 133-136 and/or 158-161 (nomenclature according to Falquet et al., 2002). Further preferred phosphorylation sites are located at amino acids 12-14, 30-32 and/or 85-87. Further potential modification sites are amidation sites, preferably located at positions 22-25 and/or 30-33, glycosylation sites at positions 150-153, 156-159 and/or 204-207, and myristylation sites, preferably located at positions 94-99, 149-154, 168-173, 175-180 and/or 202-207 according to the nomenclature of Falquet et al. 2002.

In the following, the relevance of the experimental data according to the present application are explained with regard to preferred medical indications.

Schizophrenia

Schizophrenia is a serious and disabling mental disorder with symptoms such as auditory hallucinations, disordered thinking and delusions, avolition, anhedonia, blunted affect and apathy. Epidemiological, clinical, neuropsychological, and neurophysiological studies have provided substantial evidence that abnormalities in brain development and ongoing neuroplasticity play important roles in the pathogenesis of the disorder (Arnold et al. 2005).

Schizophrenia is thought to include a disorder of dopaminergic neurotransmission, but modulation of the dopaminergic system by glutamatergic neurotransmission seems to play a key role. This view is supported by genetic findings of the neuregulin- and dysbindin genes, which have functional impact on the glutamatergic system (Muller and Schwarz 2006). What has become increasingly clear is that several regions that are likely to contain genes (including neuregulins) contributing to schizophrenia are also relevant to bipolar affective disorder, a finding supported by recent twin data (Farmer et al. 2007; Owen et al. 2007).

Neuregulin-1, which is a psychosis susceptibility gene with effects on neuronal migration, axon guidance and myelination that could potentially explain findings of abnormal anatomical and functional connectivity in schizophrenia and bipolar disorder (McIntosh et al. 2007).

There is an ever increasing body of evidence of a genetic linkage of Neuregulin 1 to schizophrenia (review: Farmer et al., 2007). The enhancement of glutamate, GABA and nicotinic neurotransmission by Neuregulin-1 (Fischbach 2007; Woo et al. 2007; Li et al. 2007) is relevant in this context, as well as implication with brain inflammation (Hanninen et al. 2007).

The regulation of 3-hydroxy-3-methylglutaryl-Coenzyme-A reductase, the rate-limiting enzyme for cholesterol biosynthesis (Pertusa et al. 2007), important for myelinisation, is assumed to have implications in this condition as well.

The fact that among genetic risk factors common to schizophrenia, bipolar disorder and depression, NRG1 plays an outstanding role, has triggered suggestions that genes implicated in these psychoses such as NRG-1 may eventually provide the basis for classification based on biology rather than symptoms, and lead to novel treatment strategies for these complex brain disorders (Blackwood et al. 2007; Bertram et al. 2007).

The experimental data of the present application demonstrate the effectiveness of administration of a soluble recombinant Neuregulin-1 β isoform in an experimental model of schizophrenia.

Alzheimer's Disease

Initial research by the inventors showed that Neuregulin 1 β is diminished in post mortem sections of hippocampi of brains of Alzheimer's patients as compared to age-matched controls (Sommer et al., 2004) with a clear positive correlation of the soluble fragment of Neuregulin-1 with learning performance in a radial maze test (Sommer et al., 2004).

There are numerous reports demonstrating the role of NRG-1 in activity-dependent synaptic changes (Xie et al. 2006; Kwon et al. 2005; Rimer et al. 2005; Bao et al. 2004; Yang et al. 2005) important for learning and memory (Ozaki et al. 1997; Ozaki et al. 2004; Golub et al. 2004; Schillo et al. 2005b). As shown below, the NRG1 β fragment containing the extracellular domain was clearly associated with learning in a behavioural animal model. Showing decreased expression of the protein in post mortem brain slices of the hippocampal regions (responsible for short term memory formation) of Alzheimer patients as compared to age-matched controls could demonstrate the absence of memory-related synaptic activity, in regions of apparently still healthy neurons.

Very recent discoveries (Hu et al. 2006; Glabe 2006; Schubert 2006) show that NRG 1 is processed by BACE1 (13 secretase), an enzyme that helps generate clumps of amyloid-β in the brains of people with Alzheimer disease, which explains the link to Alzheimer's disease, its concomitant role in myelin formation relates to the neurotrophic properties of NRG 1 (Hu et al., 2006; Glabe 2006; Schubert 2006). The enzyme, BACE1 (beta-site amyloid precursor protein—cleaving enzyme 1), is required to cleave amyloid-β from a larger precursor. (After BACE1-mediated cleavage, the presenilin-containing complex γ-secretase makes the final cleavage, liberating amyloid-β.

The cleavage of NRG by secretases is crucial for nerve myelination. Just like amyloid precursor protein, neuregulin 1 is also cleaved by β-secretase. Proteolytic cleavage of neuregulin 1 by β-secretase is critical for peripheral nerve myelination by Schwann cells. Drugs that target β-secretase could affect peripheral nerve development and function.

The in initial observation was by the group of Haass (Willem et al. 2006), who found that BACE1 seems also to be required for myelination. Peripheral nerve myelination occurs early in life, so it is unclear how BACE1 inhibition might affect older animals. There are indications that BACE1 also has a role in myelination of the central nervous system. Transgenic animals deficient in BACE-1 had myelin defects in the peripheral nerves Also in the context of neurodegeneration and Alzheimer's disease, the recent discovery of enhancement of glutamate, GABA and nicotinic neurotransmission by Neuregulin-1 (Fischbach 2007; Woo et al. 2007; Li et al. 2007) is relevant.

The experimental data of the present application demonstrate the effectiveness of administration of a soluble recombinant Neuregulin-1 β isoform in an experimental model of Alzheimer's disease.

Stroke, Traumatic Brain Injury

A series of stroke-related in vivo experiments by independent external research in the US, demonstrate neuroprotection by Neuregulin 1 which by itself is antiapoptotic (Xu et al., 2004, 2005 and 2006; Guo et al., 2006)

NRG-1 reduces neuronal damage and improves neurological outcome after middle cerebral artery occlusion (a common stroke model) (Xu et al. 2005b; Xu et al. 2004; Xu et al. 2006; Guo et al. 2006).

In the same study about the therapeutic efficacy and mechanism of recombinant human NRG-1 in attenuating brain injury by ischemia/reperfusion, it was found that NRG is antiapoptotic. NRG-1 (3.0 ng/kg) was applied intravascularly 10 min before middle cerebral artery occlusion (MCAO) and subsequent focal cerebral ischemia for 90 min and reperfusion for 24 h.

The data of the present invention demonstrate that administration of recombinant soluble Neuregulin-1 isoforms at low concentration has a significant pharmacological effect and thus is assumed to be effective in models of stroke and traumatic brain injury.

In the following, the present application is explained in more detail by the Figures and Examples given herein below.

NRG are key parts of functional complexes, consisting at least of neuregulins (NRG), receptor tyrosine kinases (ErbB receptors), heparansulfate proteoglycans (HSPG) and NMDA receptors (NMDAR), which are transiently and activity-dependent assembled together in cholesterol (CHO)-rich membrane microdomains. In particular the shaping of calcium signals is important for the interaction with subsynaptic scaffolding proteins by posttranslational modifications (PSD-95, by interaction with certain phosphorylated domains, like PDZ- or SH-domains on partner proteins). The PSD-95 complex directly regulates pro-inflammatory enzymes like nitric oxide synthase (NOS, iNOS is inducible, nNOS is neuronal) and Cox-2 (cyclooxygenase-2), which promote their effects in a complex relationship with related, but not necessarily downstream mechanisms, involving NADtdependent enzymes like PARP-1 (poly-ADP-ribose polymerase-) and Sir-2 (sirtuin-2); PARG is poly(ADP-ribose) glycohydrolase the complementary and antagonistic enzyme to PARP-1, HDAC are histone deacetylases, the general class of enzymes which includes Sir-2. MPTP stands for the mitochondrial permeability transition pore. DRP-2 is dihydropyrimidinase-related protein 2. Also other important membrane proteins, like certain nicotinic acetylcholine receptors (nAChRa7), GABAA receptors (GABAAR) amyloid precursor protein (APP) and proteases (PS) are transiently organized in lipid rafts and acquire different functional properties outside the usual phospholipid (PL) environment, details in (Schrattenholz and Soskic 2006).

Figure 1:
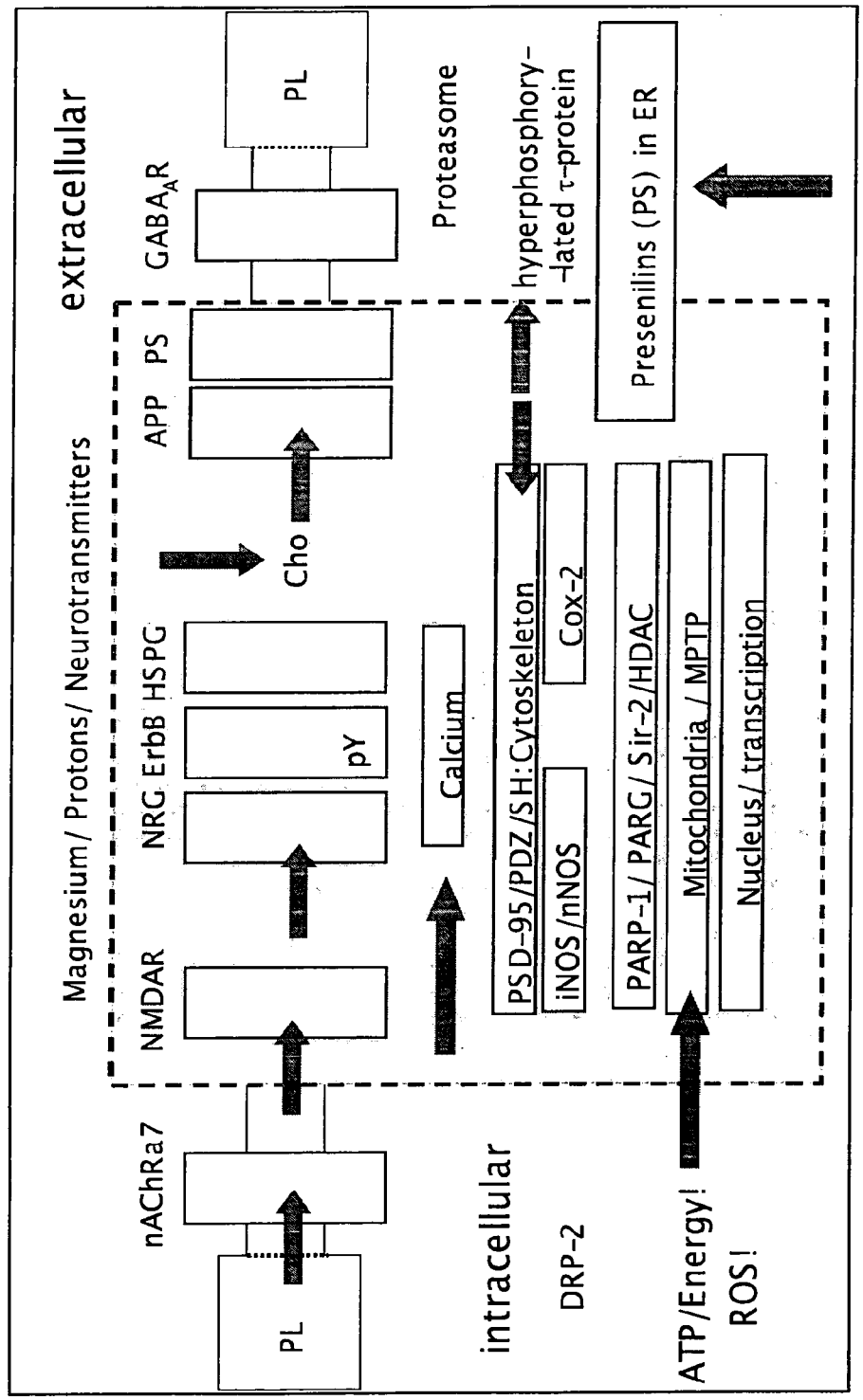
FIG. 1: Various reviews and numerous research articles on Neuregulin 1 show the key functional position of NRG 1 as an upstream regulatory principle of mechanisms thought to be pivotal in neurodegenerative diseases, neurological disorders, as well as physiological function.
Figure 2:
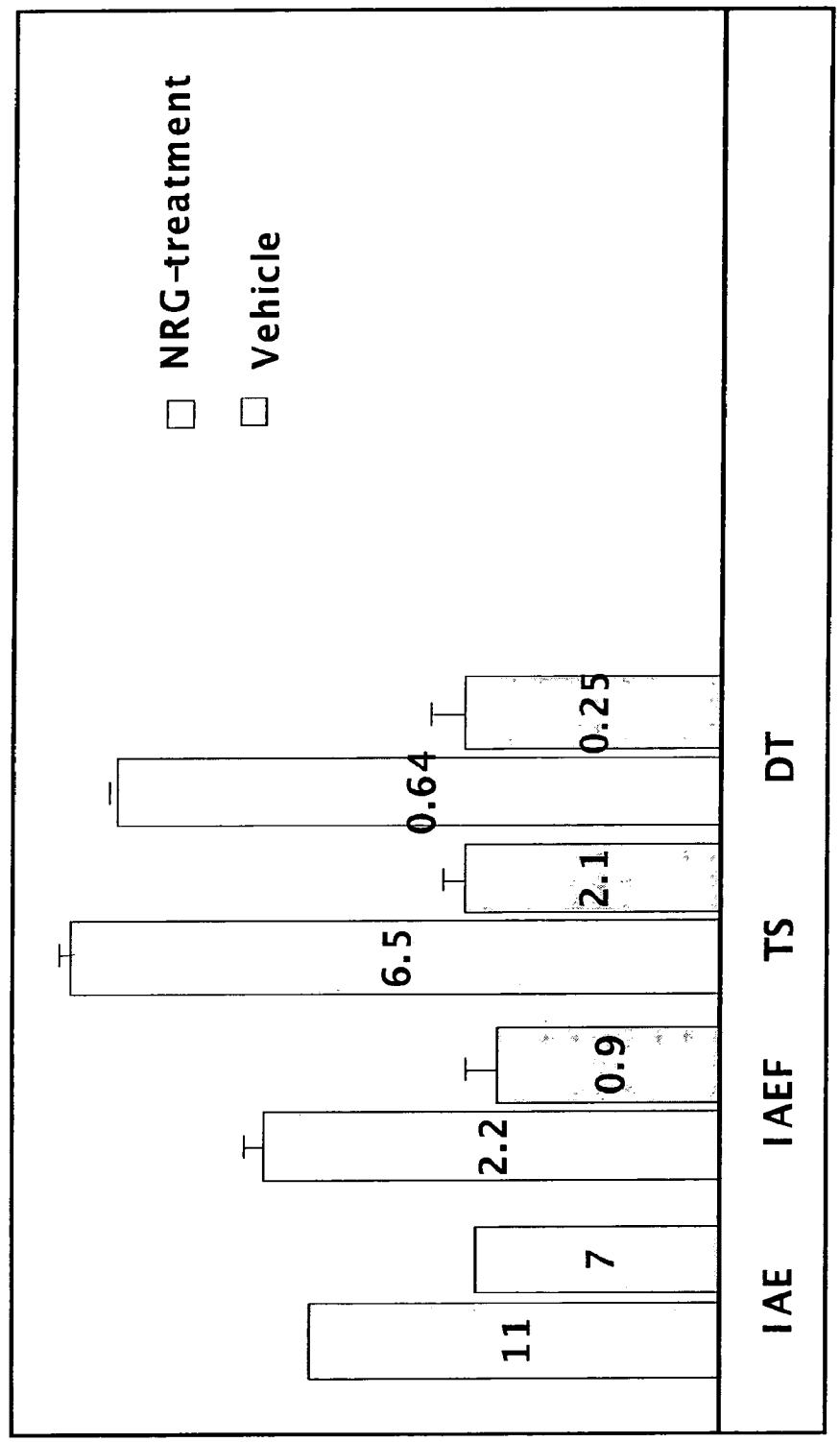

FIG. 2: Summary of learning experiments in Morris water maze: animals treated with a daily dose of 3 ng/kg (i.v.) of the soluble extracellular domain of neuregulins-1 beta (NRG-1 beta-ECD) were significantly better in learning than vehicle treated animals; IAE: inner area entry; IAEF inner area entry frequency; TS: time spent in inner area; DT: distance travelled in inner area.

Figure 3:
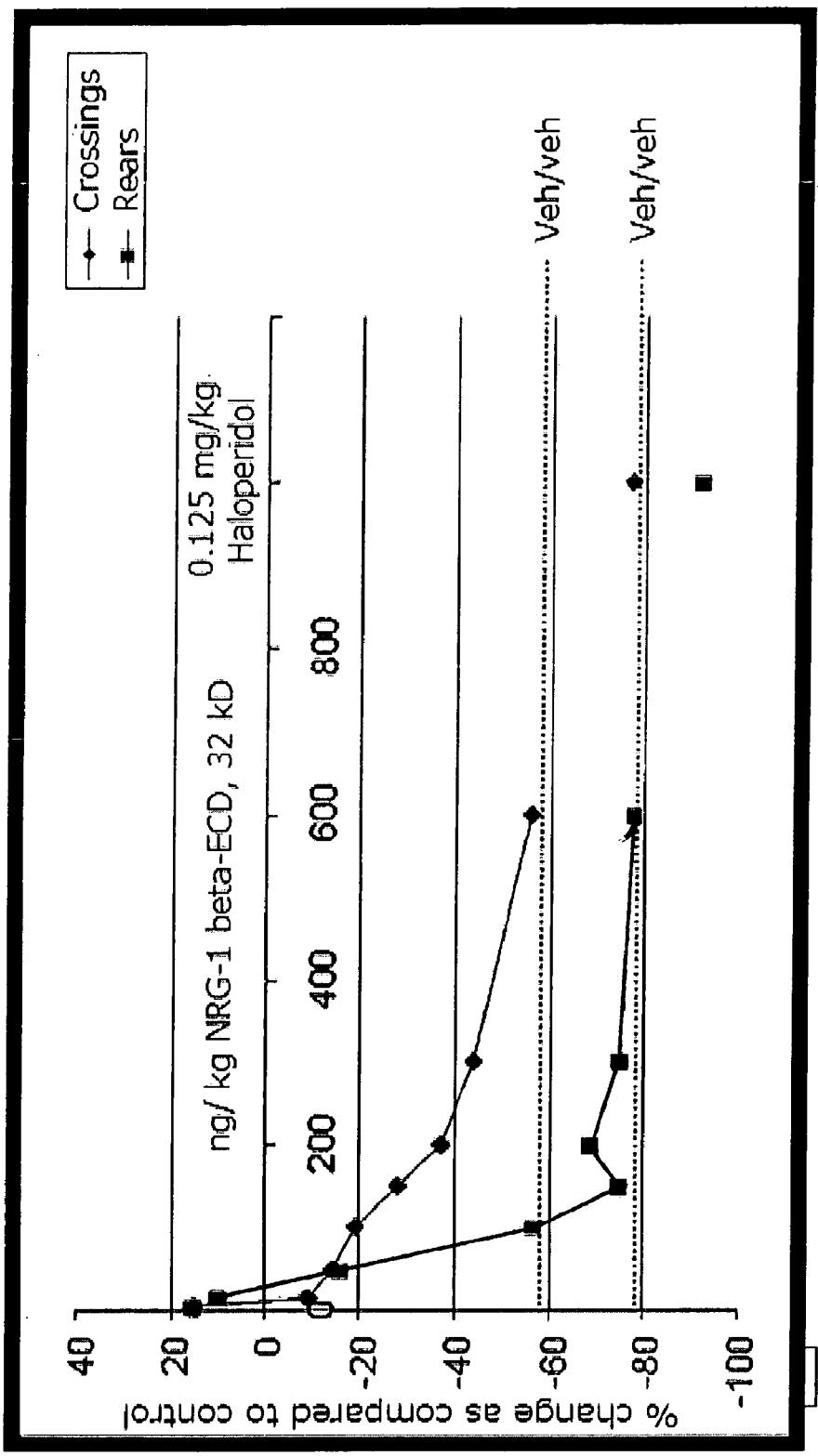
Figure 4:
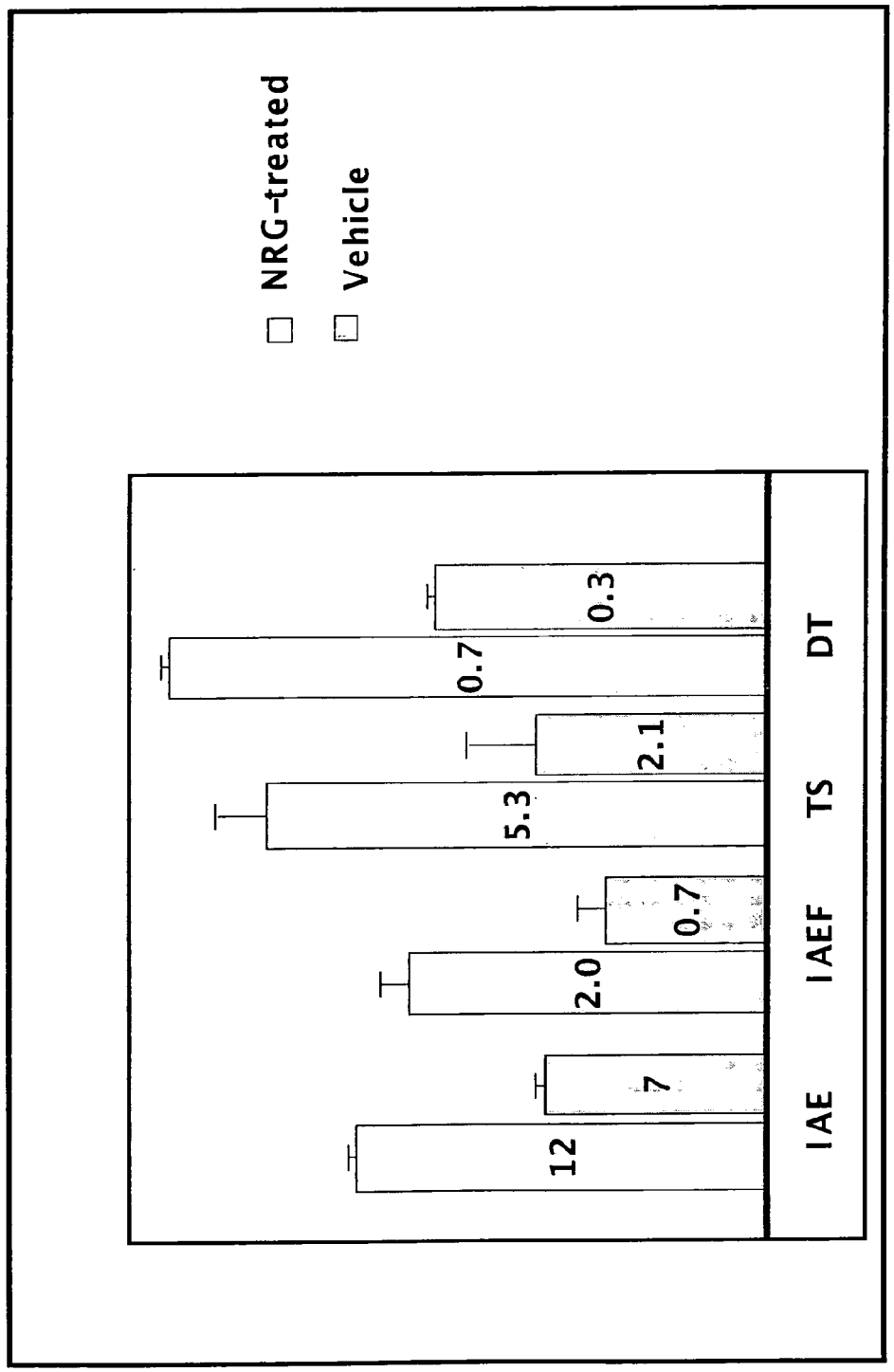

FIG. 3: Reduction of Amphetamine-induced hyperactivity by NRG-1 beta-ECD, a widely accepted model for schizophrenia. Concentrations ranged from 15 to 600 ng/kg (i.v. injection 15 minutes prior to amphetamine application). A positive control of 0.125 mg/kg Haloperidol was included. Whereas Haloperidol like other non-typical and typical antipsychotics usually reduce activity below control level (indicated here by dotted lines labelled veh/veh, in blue for crossings and in magenta for rears), NRG-1 beta-ECD reduction asymptotically approaches control levels of activity, but does not cause further reduction. The low effective concentrations of NRG-1 beta-ECD and the absence of negative effects (reduction of activity below vehicle control levels) are the outstanding properties in this model. The effects are significant with $p<0.05$;

FIG. 4: Summary of learning experiments with APPPS mouse model of cerebral amyloidosis and Alzheimer's disease in a Morris water maze: animals treated with a daily dose of 200 ng/kg i.p. NRG-1 beta-ECD were significantly better in learning than vehicle treated animals; IAE: inner area entry; IAEF inner area entry frequency; TS: time spent in inner area; DT: distance travelled in inner area.

Figure 5:
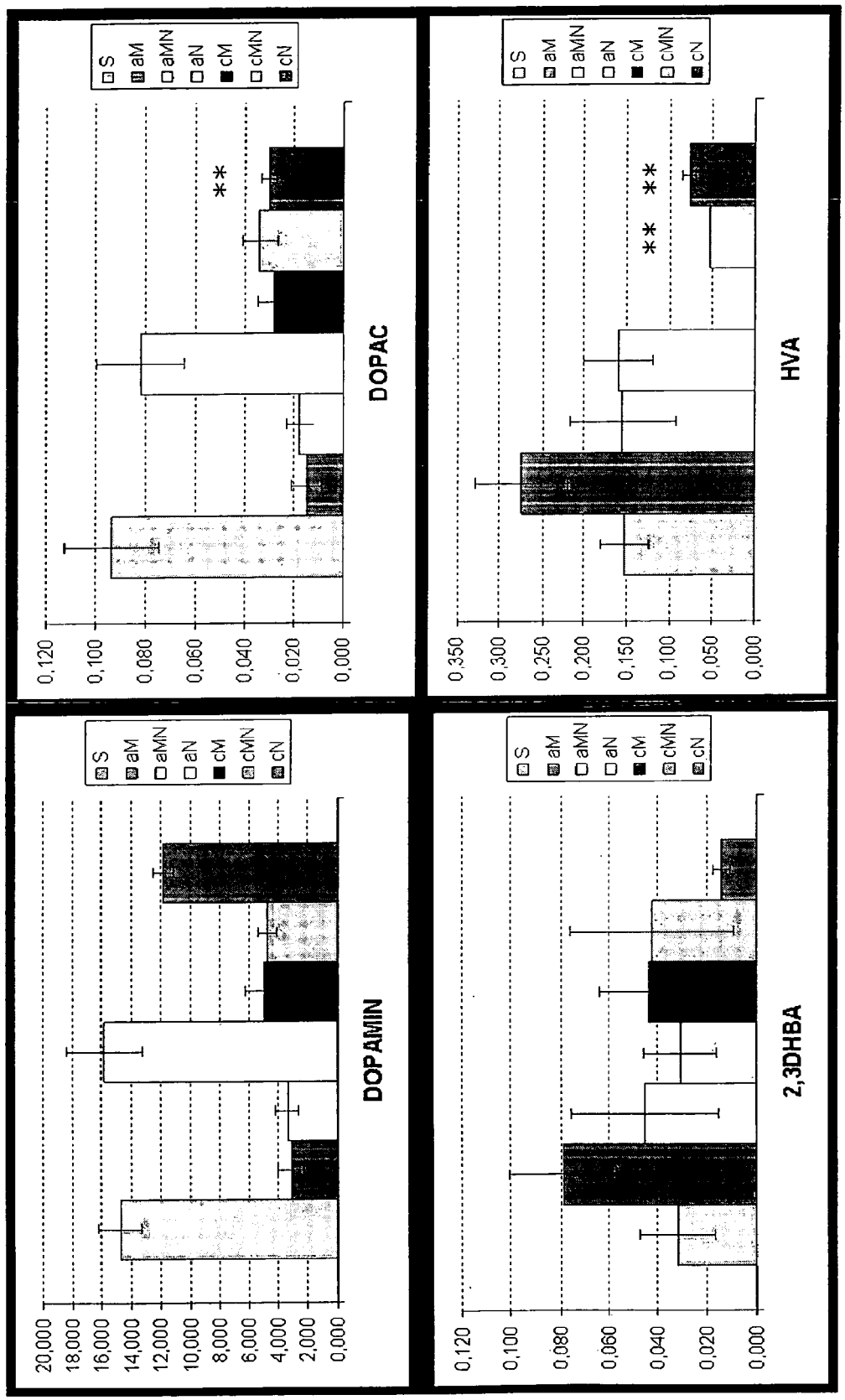

FIG. 5: HPLC quantification of dopamine and its metabolites: The columns labelled with asterisks are highly significant.

| Legend | S | Saline (control) |
|---|---|---|
| | aM | acute MPTP |
| | aMN | acute MPTP and NRG-1 beta-ECD |
| | aN | acute NRG-1 beta-ECD |
| | cM | chronic MPTP |
| | cMN | chronic MPTP and NRG-1 beta-ECD |
| | cN | chronic NRG-1 beta-ECD |

Figure 6:
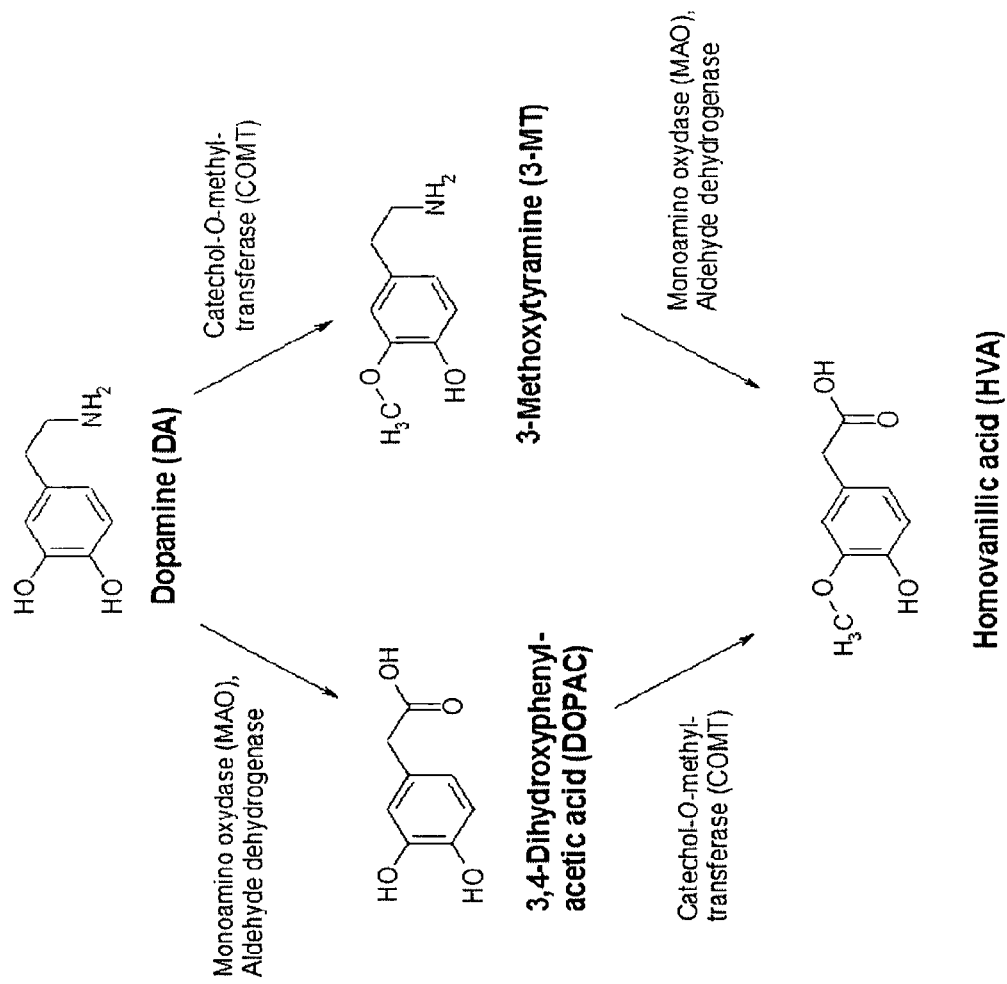

FIG. 6: Metabolism of dopamine by MAO-B and COMT.

Figure 7:
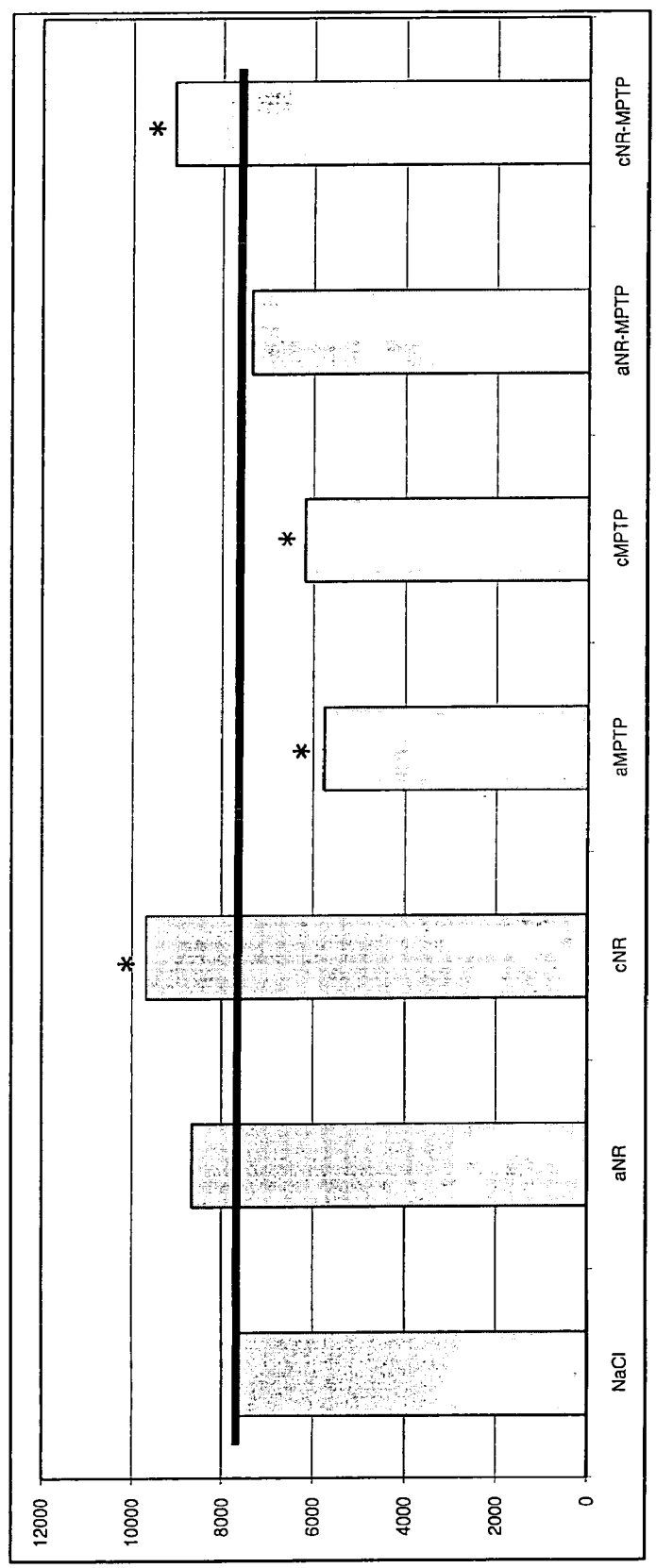

FIG. 7: MPTP exposition leads to a significant loss of dopaminergic neurons in the *Substantia nigra* (aMPTP, $p=0.0005$; and cMPTP, $p=0.0075$). The ip application of 20 ng/kg of NRG-1 beta-ECD leads to a reversal (aNR-MPTP; $p=0.57$, i.e. not different from vehicle control) or clear and significant improvement of the MPTP lesion (cNR-MPTP; $p=0.0097$); in the chronic model (5 days daily ip application of 20 ng/kg of NRG-1 beta-ECD) there is also a significant effect number of dopaminergic neurons (cNR; $p=0.0002$);

| Legend | NaCl | Saline (control) |
|---|---|---|
| | aMPTP | acute MPTP |
| | aNR-MPTP | acute MPTP and NRG-1 beta-ECD |
| | aNR | acute NRG-1 beta-ECD |
| | cMPTP | chronic MPTP |

| Legend | NaCl | Saline (control) |
|---|---|---|
| | cNR-MPTP | chronic MPTP and NRG-1 beta-ECD |
| | cNR | chronic NRG-1 beta-ECD |

Figure 8:
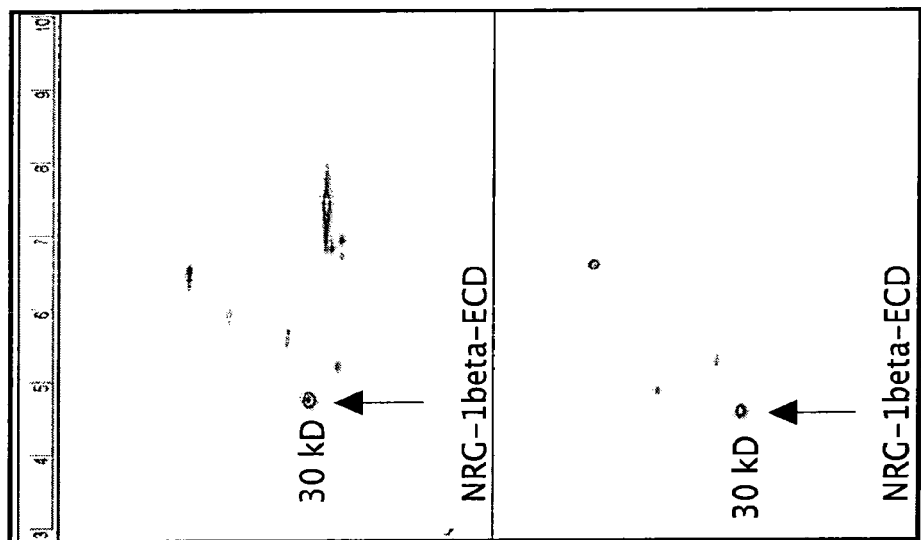

FIG. 8: Two representative images of 2D-Western blots of brain proteins of APPPS mice stained for Neuregulin-1 β are shown of each, a treated and good learning animal (top) and non-treated animal with inferior learning performance (below).

The numbers in the upper part are pI values of the 2D gel.

Figure 9:
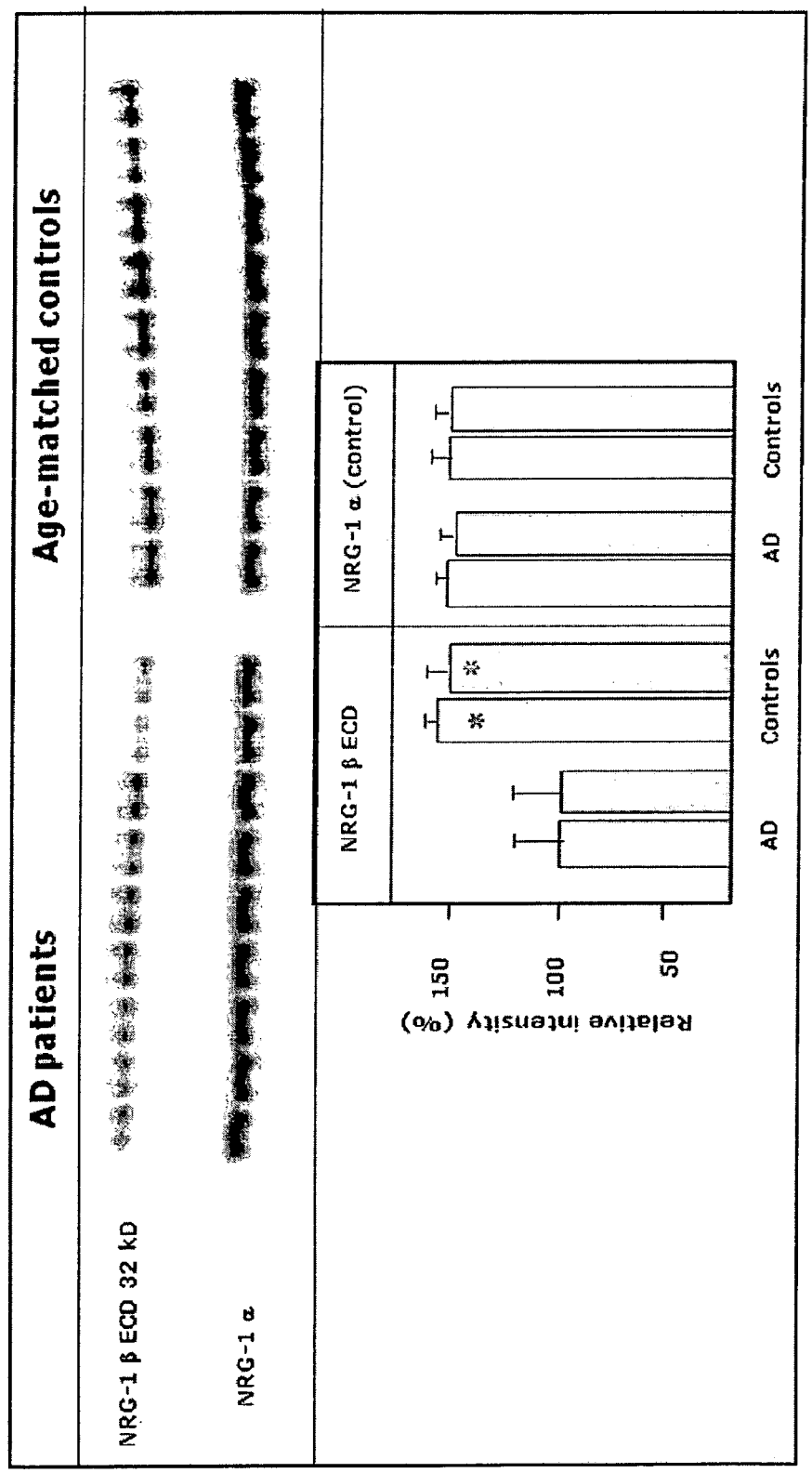

FIG. 9: A Western blot experiment compairs the abundance of the NRG-1B ECD-fragment in post mortem cortical material from Alzheimer patients and controls.

Figure 10:
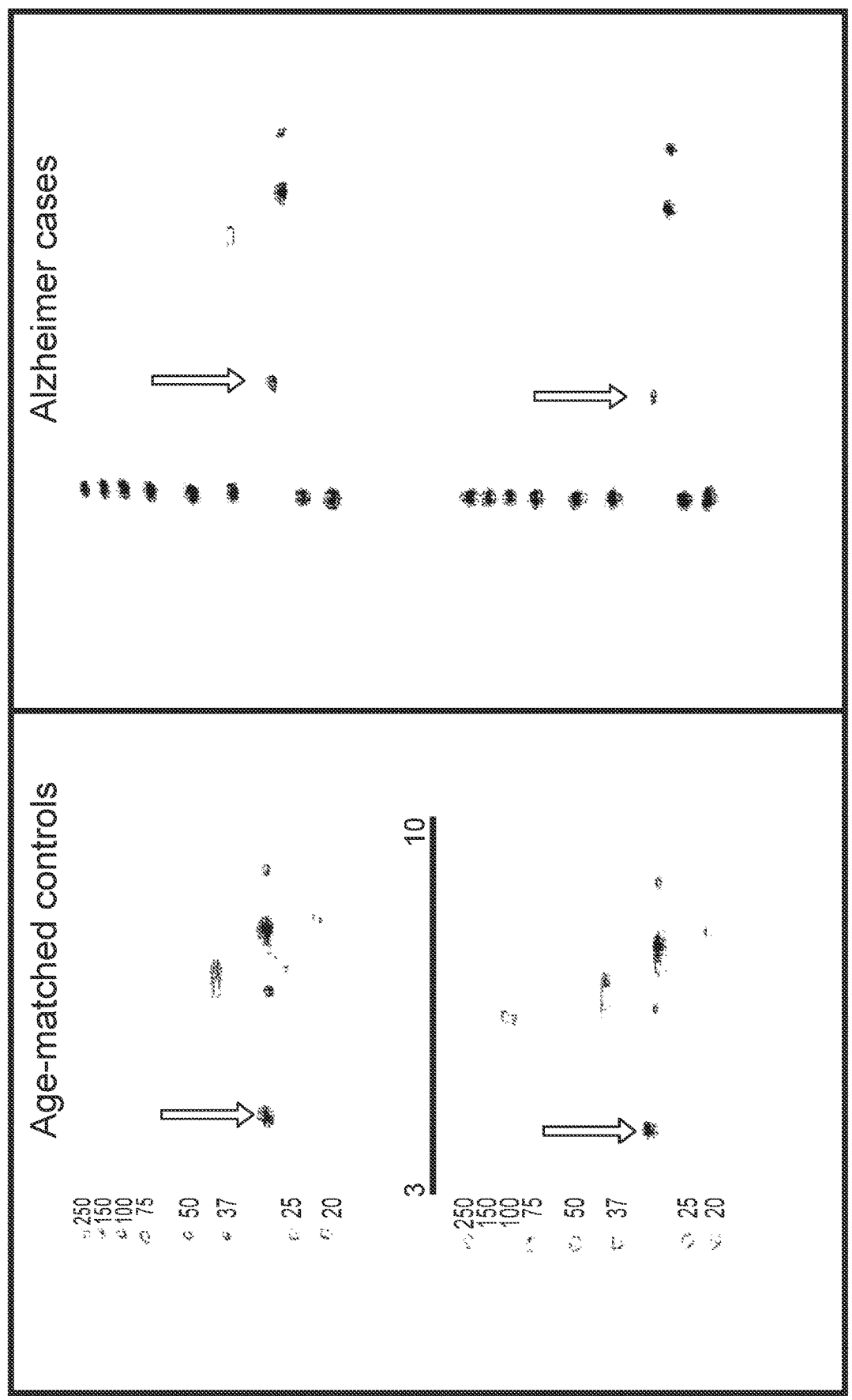

FIG. 10: 2D-PAGE shows, that the acidic isoform of NRG-1 β-ECD, with a pI of approx. 5-5.5 and a molecular weight of approx 25-32 kD in these experiments is clearly diminished in Alzheimer's patients brains.

Figure 11:
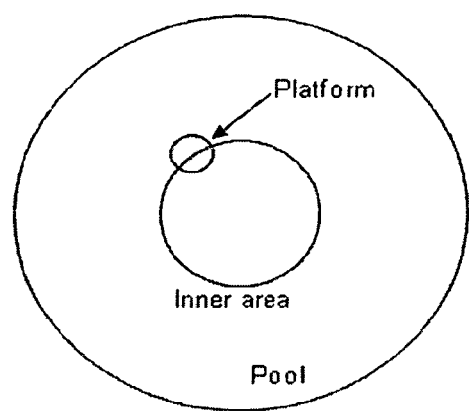

FIG. 11: is a schematic of the pool used for the Morris Water Maze assessment.

Figure 12:
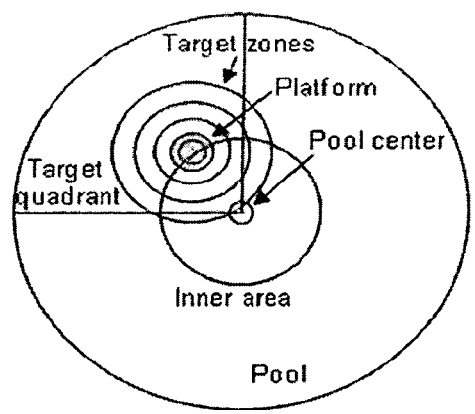

FIG. 12: is a schematic of the pool used for the Morris Water Maze assessment showing the zones for computing the animals' track records.

DETAILED DESCRIPTION OF THE INVENTION

Examples

General:

In all of the following experiments fragments of Neuregulin-1 beta have been used, comprising only the extracellular domain (ECD) of the entire transcript of the human nrg-1 gene. They had a molecular weight of approx 25-32 kD and isoelectric points between approx 5 and 9.5, depending upon phosphorylation and/or glycosylation status.

The physiologically active form of Neuregulin-1 isoform has a pI of approx. 5.5. The physiologically active form has an pI of approx. 5.5 (most of the experiments were carried through with a commercially available isoform produced in *E. coli*, with a molecular weight of 26 kD and an pI of approx. 9.0)

This isoform is a recombinant soluble human NRG-1 beta fragment consisting of the first 245 amino acids of NRG-1B, purchased from R & D Systems, Inc. (Catalog No. 377-HB-CF). It will be named NRG-1 beta-ECD in the following. This active isoform has a pI of approx. 9.0

We also tested a corresponding fragment of NRG-1B with 8 kD, only comprising the EGF domain, purchased from R&D Systems (Catalog No. 396-HB). This fragment appears to be neuroprotective as well in vitro and in vivo, but was not investigated in depth because of much higher proliferative properties, which raised concerns about cancerogenity.

Example 1

Initial Toxicology Data Indicate that NRG1β (ECD) has No Adverse Effects in Acute Toxicology and In Vitro Mutagenicity Tests.

There was no acute intravenous toxicity in rats: All animals survived until the end of the study period. No clinical signs were observed during the course of the study. The body weight of the animals was within the range commonly recorded for this strain and age. No macroscopic findings were recorded at necropsy. The median lethal dose of NRG1β (ECD) after single intravenous administration to female rats, observed over a period of 14 days is: $LD_{50}$ (female rat): greater than 5000 ng/kg body weight.

Daily intravenous administration of Neuregulin over a period of seven days at dose levels of 50, 200 and 600 ng/kg body weight/d did not result in any premature death. No clinical signs were recorded. The treatment did not affect the food consumption and body weight development. The no observed effect level (NOEL) was established at 600 ng/kg body weight/d.

In the mouse lymphoma thymidine kinase locus assay using the cell line L5178Y according to the OECD Guideline for the Testing of Chemicals, No. 476 "In vitro Mammalian Cell Gene Mutation Test", NRG1β (ECD) was non-mutagenic.

In the chromosome aberration test in Chinese hamster V79 cells according to the OECD Guideline for the Testing of Chemicals, No. 473, NRG1β (ECD) did not induce structural chromosome aberrations.

Moreover, in none of the animal experiments carried out with regard to efficacy (some of them going on for several months with daily iv applications) did we ever observe adverse effects of NRG1β (ECD).

Application of NRG1β (ECD) in the various animal models described below, was either by intravenous (iv) or intraperitoneal (ip) injections; concentrations were ranging from 3-600 ng/kg.

Example 2

Learning and Memory: Spatial Learning with and without NRG-1 Beta-ECD Application Methods:

The Morris Water Maze assesses spatial learning. It requires animals to swim in a water-filled pool and to find a rescue platform submerged just below the surface. It is obligatory that the platform is placed away from the walls of the maze and that animals have reference points visible from the water surface that permit estimation of location, but are not close enough to the target to permit associative learning. The animals are trained that rescue only comes via the platform meaning that all animals which do not find the platform, are guided to the platform and allowed to rest before being removed from the set-up. Therefore, one of the most important reference points for the mouse is the human operator.

The experiment aims at determining two key parameters associated with murine spatial recall:
 the rate at which the mice learn to relocate the platform
 the ability to retain the information in the short term (within a training period or overnight)

Animals

The study is performed with two groups of APP/PS mice (Meyer-Luehmann et al. 2006; Radde et al. 2006), one of which is treated by a daily dose of NRG-1 beta-ECD and the other one is sham treated as a control. Each group consists of 8 males which are nine weeks old at the beginning of their first series of experiments.

The first series of experiments started with two subgroups of 8 treated and 8 untreated mice on week 42 and will last for 15 days. Further series of identical experiments will be performed 6, 12, etc. weeks later.

For a second pair of subgroups (8 treated and 8 untreated nine weeks old males) the same series of experiments started on week 48, so the experiments of these subgroups lag exactly 6 weeks behind the ones of the first subgroups.

Apparatus

The learning aptitude of the treated and untreated APP/PS mice is assessed using a circular Morris water maze which should be large enough to provide searching space without exhausting the mouse. Utmost care needs to be taken to keep each detail of the experimental setup as invariable as possible throughout all experiments.

In the current study, a pool of 120 cm diameter is used which is placed at an exactly reproducible position in the lab with always identical orientation. At fixed positions in the pool, a white, translucent, circular platform of 15, 10, or 5 cm diameter is placed that extends to just below the water surface (so it is invisible to the mice) and that the animals can climb on—which is the only means to rest out of the water. To assist climbing, the platform is coated with a gauze grip surface (see FIG. 11).

In order to perform the rescue procedure in probe trials as detailed below, the platform is equipped with a mechanism that allows for automatically raising and lowering it without direct operator intervention. Thus, depending on its height the platform is accessible to the swimming mice or not "On-demand platform" (Buresova et al. 1985).

Platform locations are always situated in a ring shaped, concentric region of the pool with inner and outer diameters ~40 cm and ~80 cm, respectively. Four quadrants are defined such that the platform occupies the central region of one of them (the target quadrant). For further details on platform sizes and positions see below.

In order to make sure that platform position is exactly the same throughout an entire series of experiments; a socket will be firmly affixed to the floor of the pool on which the platform can be mounted with a minimum of spatial tolerance. On top of the platform, in its center, there is another mounting for a (proximal) cue sticking out of the water which is well visible on the video recording as well as to the mice swimming in the pool. For a check of platform position, a brief video recording will be taken without an animal but with the cue plugged into the platform whenever the platform or the video camera have been manipulated with in any way.

The water is made opaque using low fat milk powder. The water temperature should be cold enough to encourage searching for an exit but not so cold that the animals suffer or are exhausted. As a fair compromise, water temperature is monitored at the start of each experiment and modulated with either warm water or ice flakes to 18° C. Between individual trials, temperature is readjusted as needed.

Four distal cues (of different simple geometric shapes and different colors, height ~20 cm) are attached ~20 cm above the sides of the pool, one in each quadrant. Care is taken to place each cue in exactly the same location throughout all experiments. The entire pool is enclosed by a white translucent curtain. Lighting is dimmed and diffuse.

A video camera is firmly mounted at an exactly vertical position above the center of the pool, such that the pool completely fills the video image. Video recordings are taken at PAL resolution (720×576 pixels, 25 frames per second), at the least. The videos are evaluated by an automatic tracking system that allows for flawless detection of the animals movements with time.

Mice are placed into the water using a special devise that is mounted on a stick, so they can be watered at exactly defined spots along the rim of the pool without the operator entering the cabin made up of the translucent curtain.

Experimental Design

In each session, mice are placed into the pool at predefined sites and are allowed to swim for 60 s. Animals' motion tracks are recorded by a video tracking system, and parameters are computed from which conclusions regarding the animals' learning aptitude can be drawn (most notably the period until the mouse hits the platform for the first time="escape latency"; further details see below). If a mouse succeeds in finding the platform it is left resting there for a short period of time (~15 s). Otherwise, after 60 s of swimming, the mouse is guided to the platform by the operator and allowed to rest for ~15 s. Afterwards, it is picked up by the operator, dried gently and returned to its housing or prepared for the next swim.

On each day of experiments, one trial per mouse is performed in the early morning. Each trial consists of two consecutive swims originating from two different quadrants, but never from the target quadrant. Exact watering sites (and platform positions whenever applicable) are assigned randomly for each swim of each day, but do not differ between the individual mice during that day.

If mice turn out to learn extremely slowly the number of swims per trial or trials per day may be increased (and vice versa). Moreover, in many mouse strains younger animals learn very quickly, so after four or five days of training, escape latencies remain constant at a few seconds only which is equally true in treated as in untreated animals. However, for the statistical evaluation, it is of advantage if the curve of escape latencies over training days does not saturate but rather decreases monotonically. Therefore, an experimental design is used in which the problem to solve becomes more difficult with training progress: On predefined days the platform is replaced with a smaller one while the platform's center coordinates remain the same. If and when platforms are swapped may be determined independently for each series of experiments and ought to depend on the outcomes of the preceding series.

In each series of experiments mice are subjected to three different kinds of tasks:

Cued place navigation. The platform is marked with a cue, and the mouse is allowed to swim until it finds the platform. This procedure tests associative learning and serves for dividing mice into two experimental groups the learning aptitudes of which are as similar as possible. Moreover, in the second and further series of experiments, cued place navigation supports blanking recollection of the position of the platform in preceding series.

Hidden platform acquisition training. The platform is invisible to the mouse and located at the same position as during the preceding swim. This task allows for monitoring the mouse's progress in recalling the exact location of a hidden platform ("spatial learning").

Probe trial testing. In this task, the on-demand platform is maximally lowered underneath the surface and the mouse is allowed to swim freely searching for it. Probe trial testing assesses the animals' absolute recall which, in this context, can be also interpreted as conviction, persistence or certainty regarding the platform location. The conventional approach to interpreting the experiment is that animals that have firmly fixed the location of the platform will more persistently search in a limited location and thus spend more time in the zone next to the platform.

In probe trial testing, there is a risk that the inability to find the plat-form may reduce the incentive to swim to the platform zone. In order to keep these irritations as small as possible, the modalities of human rescue ought to remain the same so there is some spatial constancy despite the absence of the platform. Therefore, after 60 s of swimming the platform is lifted to just beneath the surface, the mouse is guided there by the operator and allowed to rest for ~15 s before being taken out of the apparatus.

On all days of probe trial testing, only one swim is performed.

Approximately 60 minutes prior to each trial, mice are treated daily with either 5 ng/kg NRG-1 beta-ECD (suspended in black 6 mouse serum and provided i.v. in a volume of 20 μL per mouse) or with 20 μL of vehicle i.v., respectively.

On day 1 of the first series of experiments, all mice in the study receive sham treatment only. Thereafter, mice are assigned to the Neuregulin and the control groups such that the distributions of escape latencies match in both groups.

In each series of experiments the following chronology is adhered to:
- day 1. Cued platform search with platform of size 10 cm and position changing for each swim.
- day 2. Cued platform search with platform of size 10 cm and position changing for each swim.
- day 3. Cued platform search with platform of size 10 cm and position changing for each swim.
- day 4. Cued platform search with platform of size 10 cm and same position as the last one on day 3.
- day 5. Hidden platform search with platform of size 15 cm and same position.
- day 6. Hidden platform search with platform of size 15 cm and same position.
- day 7. Hidden platform search with platform of size 15 cm and same position.
- day 8. Hidden platform search with platform of size 10 cm and same position.
- day 9. Probe trial testing.
- day 10. Hidden platform search with platform of size 10 cm and same position.
- day 11. Hidden platform search with platform of size 10 cm and same position.
- day 12. Hidden platform search with platform of size 5 cm and same position.
- day 13. Hidden platform search with platform of size 5 cm and same position.
- day 14. Hidden platform search with platform of size 5 cm and same position.
- day 15. Probe trial testing.

It may be necessary to aid unlearning of the platform position from a preceding set of experiments by allowing the mice to freely swim for a few days without platform present.

The rate of learning is assessed by monitoring each training/test session and noting the success of the animals in finding the platform as well as the evolution of the search strategy from skirting the sides of the pool to moving away from the sides to search in the near to central area where the platform lies.

Measured Parameters

From the animals' video recordings, each mouse's motion track is extracted and exported as a series of x, y, and time coordinates for further processing. Care needs to be taken to reliably identify each track's staring point and to avoid tracking errors.

Simultaneously, a number of parameters are computed from which conclusions regarding the animals' learning aptitude can be drawn (see below). Parameter recordings are halted after 60 s or if the mouse has found the platform (whichever happens earlier).

For the definition of parameters to be computed from the animals' track records the following zones are defined (see FIG. 12):

In order to keep evaluations as flexible as possible, four concentric target zones (centered about the platform) of 5.5 to 30 cm diameter are employed.

Parameters computed from the animals' track records include:
- Total distance travelled
- Overall average speed
- Number of entries to the pool center
- Time in the pool center
- Latency to first entry to the pool center
- Distance travelled to first entry to the pool center
- Number of entries to the inner area
- Time in the inner area
- Distance travelled in the inner area
- Latency to first entry to the inner area
- Distance travelled to first entry to the inner area and for each target zone 1 to 4 and the target quadrant
- Number of entries to the zone
- Time in the zone
- Distance travelled in the zone
- Latency to first entry to the zone
- Distance travelled to first entry to the zone
- Distance from beginning of track to nearest point of zone
- Average distance from the zone when outside the zone
- Minimum distance from the zone when outside the zone
- Time to minimum distance from the zone when outside the zone
- Time getting closer to the zone
- Time getting further away from the zone
- Time moving towards the zone
- Time moving away from the zone
- Number of head entries to the zone
- Time of head in the zone
- Distance of head travelled in the zone
- Latency to first entry of head to the zone
- Average distance of head from the zone when outside the zone
- Minimum distance of head from the zone when outside the zone
- Initial heading error
- Average heading error
- Number of exits from the zone For each day of the experiment, the readings of parameters of learning progress in the treated and untreated groups are compared to each other statistically.

On examining the track records of individual mice, a human observer is able to come to a fairly realistic perception of the animals' assertiveness in locating the platform which is not fully reflected in the measured parameter values. Therefore, track records are also manually inspected and the animals' recall of the platform position is rated.

Results:

Those animals treated with a daily dose of 3 ng/kg NRG-1 beta-ECD i.v. 30 min prior to training were significantly better in learning-related parameters than the vehicle treated group.

Neuregulin not only improved learning, but treated animals had also developed more advanced search strategies: More treated animals entered the inner area of the pool (11 vs. 7, p=0.019), entries to the inner area occurred more often (2.17 vs. 0.92 times, p=0.02), time spent and distance travelled in the inner zone was longer (6.51 s vs. 2.13 s, p=0.09 and 0.64 m vs. 0.25 m, p=0.031, respectively).

The results of the learning experiments in a Morris water maze are summarized in FIG. 2.

Example 3

Schizophrenia: Amphetamine-Induced Hyperactivity in the Rat

Methods:

The method, which detects antipsychotic and anti-Parkinson activity, follows that described by Costall et al. 1978 and uses an activity meter similar to that described by Boissier and Simon 1966.

Amphetamine induces hyperactivity in this test situation. Hyperactivity is antagonized by classical and atypical antipsychotics acting on dopaminergic systems at the limbic level, and is potentiated by anti-Parkinson drugs.

Rats are injected with d-amphetamine (3 mg/kg i.p.) and are immediately placed in the activity meter.

The activity meter consists of 12 covered Plexiglass cages (40×25×25 cm) contained within a darkened cabinet. Each cage is equipped with two photocell assemblies at each end of the cage, 3 cm above the floor, in order to measure the number of movements by each animal (one per cage) from one end of the cage to the other. Two additional photocell assemblies are placed at 20 cm above the floor to record rearing. The scores for activity and rearing are recorded by computer over 10-minute intervals and cumulated over a 30-minute period.

15 rats were studied per group. The test was performed blind.

The test substance was evaluated at 8 doses, administered i.v. 15 minutes before amphetamine, and compared with a vehicle control group. The experiment also included a control group not treated with amphetamine.

Haloperidol (0.125 mg/kg i.v.), administered under the same experimental conditions, was used as reference substance.

The experiment therefore included 16 groups.

Data were analyzed by comparing treated groups with appropriate control using unpaired Student's t tests.

Results:

As shown in FIG. 3, NRG-1 beta-ECD in a dose-dependent manner inhibits the amphetamine-induced hyperactivity in an animal model for schizophrenia.

Conspicuously, the experiments reveal outstanding properties of NRG-1 beta-ECD:

The effects shown in FIG. 3 are strongest in the second half of the experiment (minutes 20-40). In the first 20 minutes only a smaller effect can be found, this delayed effect points to further processing of the protein.

The effective concentrations of NRG-1 beta-ECD used here are about 200-1000 times lower than those used for typical control neuroleptica like Haloperidol (125 µg/kg).

In contrast to Haloperidol, Clozapine, Olanzapine etc. there are no negative effects observed in that NRG-1 beta-ECD does not reduce activity of test animals below vehicle control levels.

Example 4

Schizophrenia: Prepulse Inhibition

Rodents with NRG1 knock-out show significantly impaired prepulse inhibition (PPI) linking NRG1 to schizophrenia. A widely used surrogate measure of psychosis in animal models, PPI is considered a schizophrenia endophenotype. It was reported that there are neurophysiological effects of missense mutations of a nonsynonymous single nucleotide polymorphism located on NRG1 (rs3924999) on PPI after extensive genotyping, in both schizophrenia and healthy control populations (Hong et al. 2007). We tested the effect of NRG-1 beta-ECD on PPI. The results so far may be summarized as follows:

At 105 dB, NRG-1 beta-ECD showed a general trend towards re-establishment of PPI (+26%, +23% and +36%, at 150, 300 and 600 ng/kg respectively), although the effect did not reach statistical significance and was not observed at 115 dB. It had no effects on spontaneous movements in the absence of stimulus at 150 or 300 ng/kg but significantly decreased spontaneous movements in the absence of stimulus at 600 ng/kg (−20% and −29%, on average and peak intensities respectively, $p<0.05$, this is similar to aripiprazole). NRG-1 beta-ECD had no effects on the reaction to the pre-pulse alone.

The results so far suggest the absence of significant effects on apomorphine-induced PPI deficits for Propsy100 over the dose-range 150-300 ng/kg and a decrease of spontaneous movements as well as a trend towards re-establishment of PPI at 600 ng/kg i.v. in the Pre-pulse Inhibition (PPI) Test in the rat (deficits induced by apomorphine).

In this series of experiments, the reference substance, aripiprazole, had weak but significant activity at 3 mg/kg i.p., but not at 10 mg/kg i.p., in the same test.

All together and under conditions used, NRG-1 beta-ECD appears to affect PPI at higher concentrations around 600 ng/kg. These results surprisingly open a novel understanding of recent neurobiological research implying (NRG1) as one of the leading candidate genes in schizophrenia.

Example 5

Learning and Memory in an Animal Model for Alzheimer's Disease (APPPS Dt Mice)

The animal experiment testing learning and memory with or without application of the soluble extracellular domain of Neuregulin 1 β (NRG-1 beta-ECD) in a Morris water maze set up described above for normal mice, have been repeated double transgenic mouse model for cerebral amyloidosis (APPPS mice(Meyer-Luehmann et al. 2006; Radde et al. 2006)).

Here again those animals which were treated with a daily dose of NRG-1 beta-ECD (here 200 ng/kg i.p. were applied) 30 min prior to training were significantly better in learning-related parameters than the vehicle treated group.

Neuregulin not only improved learning, but treated animals had also developed more advanced search strategies: More treated animals entered the inner area of the pool (12 vs. 7, p=0.009), entries to the inner area occurred more often (2.0 vs. 0.7 times, p=0.03), time spent and distance travelled in the inner zone was longer (5.3 s vs. 2.1 s, p=0.09 and 0.7 m vs. 0.3 m, p=0.025, respectively).

The results of the learning experiments with APPPS mouse model of ceretral amyloidosis and Alzheimer's disease in a Morris water maze are summarized in

FIG. 4.

Example 6

Neuregulin 1-Beta MPTP Mouse Model of Parkinson's Disease

Methods:

Male C57Bl/6 mice of 10 weeks were used in the MPTP (1-Methyl-4-phenyl-1, 2, 3, 6-tetrahydropyridine) model for Parkinson's disease.

Brain tissue is dissected (Substantia Nigra, Striatum, Cortex) of 10 weeks old male C57B16 mice (N=10 per group) at different times after treatment (0, 1, 3, 7, 21 days) with NaCl (controls) or MPTP (acute and subchronic models). The methods follow published procedures (Hoglinger et al. 2007; Hoglinger et al. 2004).

| Treatment | Time after injection of MPTP | | | | |
|---|---|---|---|---|---|
| | 0 days | 1 days | 3 days | 7 days | 21 days |
| MPTP acute | N = 10 | N = 10 | N = 10 | N = 10 | N = 10 |
| MPTP chronic | N = 10 | N = 10 | N = 10 | N = 10 | N = 10 |
| NaCl | N = 10 | | | | |

Total: N = 110

MPTP is dissolved as a powder in 0.9% NaCl and is injected intraperitoneal (acute application: 4×20 mg/kg, each at 2 hour intervals; chronic application: 5×30 mg/kg, each at 24 hour intervals). These injections take approx. 10 seconds, animals were sacrificed at defined time points (see table) by cervical dislocation. The procedures follow published protocols (Hoglinger et al. 2007; Hoglinger et al. 2004; Liberatore et al. 1999; Przedborski and Vila 2003; Vila and Przedborski 2003).

0 days after last MPTP-administration: Loss of striatal dopaminergic nerves 1 day after last MPTP-administration: Beginning microglia-activation 3 days after last MPTP-administration: Maximum of microglia-activation 7 days after last MPTP-administration: Maximum of astrocyte-activation 21 days after last MPTP-Administration: Maximum of cell death 21 days after intracerebral infusion of NRG-1 beta-ECD and a control peptide via Alzet Mini pumps, followed by MPTP treatment (acute vs. chronic), a histological quantification of dopaminergic neurons of the middle brain was performed according to stereological principles. Also, a biochemical quantification of dopamine and its metabolites in the striatum is performed by HPLC. Procedures are performed according to published protocols (Hoglinger er et al. 2007; Hoglinger et al. 2004).

| Treatment | Infusion | N |
|---|---|---|
| MPTP acute | NRG-1 beta-ECD | N = 10 |
| Control acute | NRG-1 beta-ECD | N = 10 |
| MPTP chronic | NRG-1 beta-ECD | N = 10 |
| Control chronic | NRG-1 beta-ECD | N = 10 |
| MPTP acute | Control peptide | N = 10 |
| Control acute | Control peptide | N = 10 |
| MPTP chronic | Control peptide | N = 10 |
| Control chronic | Control peptide | N = 10 |

Total: N = 80

Results:

As shown in FIG. 5, the results of the HPLC measurements of dopamine and its metabolites reveal a clear effect of administration of NRG-1 beta-ECD during MPTP insult, in this model for Parkinson's disease.

The effects are non-classical: whereas there is no significant effect upon dopamine levels, neither during MPTP-insult nor in acute or chronic controls of NRG-1 beta-ECD administration, there are pronounced and clear effects on the concentrations of DOPAC and HVA. The chronic administration of NRG-1 beta-ECD results in a clear and significant reduction of this metabolite in the absence of MPTP insult, whereas in the acute regimen only a slight decrease is observed. During the chronic condition of the MPTP insult, NRG-1 beta-ECD causes a significant increase of homovanillic acid (HVA), an effect, which is even more pronounced in the absence of MPTP-insult.

These results are can be interpreted by a down regulation of MAO-B during the chronic NRG-1 beta-ECD administration and/or COMT up regulation. Under the conditions applied a huge and significant positive effect on survival of dopaminergic neurons was observed. NRG-1 beta-ECD is also highly neuroprotective in this model. Given the ip injection during this series of experiments, the clear efficacy also proves again that NRG-1 beta-ECD is highly efficient in passing the blood brain barrier.

FIG. 6 shows the metabolic scheme which appears to be affected by NRG-1 beta-ECD administration: dopamine is converted by MAO-B to DOPAC and by COMT to 3-MT; homovanillic acid is subsequently generated form both metabolites by COMT from DOPAC and by MAO-B from 3-MT;

NRG-1 beta-ECD administration is obviously regulating activities of both enzymes.

Even more important and as shown in FIG. 7, in the MPTP model of Parkinson's disease there is a clear and significant neuroprotective effect of NRG-1 beta-ECD becoming apparent by histological quantification of dopaminergic neurons of the middle brain. The stereological method has been described elsewhere (Liberatore et al., 1999, Przedborski & Vila, 2003; Vila & Przedborski, 2003; Hoglinger et al., 2004; Hoglinger et al., 2007).

Taken together, there is a surprisingly clear and beneficial neuroprotective effect in the MPTP animal model of Parkinson's disease: The effects prove again that the intraperitoneal administration of very low concentrations of NRG-1 beta-ECD (e.g. 20 ng/kg) is sufficient to achieve efficacy and thus that NRG-1 beta-ECD passes the blood brain barrier. Also the complex influence on dopamine metabolites (HPLC results; FIG. 5) points to regulation of MAO-B and COMT by NRG-1 and NRG-1 beta-ECD.

Example 7

Identification of an Acidic Posttranslational Isoform of NRG-1 Beta-ECD as the Active Principle We have published evidence, that in learning and memory a particular posttranslational acidic isoform of NRG-1 beta-ECD is the active form (Schillo et al. 2005a). Here we show that similar patterns are observed in animal models of Alzheimer's disease and post-mortem brain tissue from Alzheimer's and Parkinson's disease patients. We conclude that this acidic isoform is the active principle.

Methods:

For staining Western blots we used the following antibodies: anti-NRG1—ECD, rabbit polyclonal (sc-28916 Lot: I 2905 Santa Cruz; H-210) Neuregulin-1 (H-210) is a rabbit polyclonal antibody raised against amino acids 21-230 mapping within an N-terminal extracellular domain of Neuregulin-1 isoform HRG-α of human origin. Neuregulin-1 (H-210) is recommended for detection of Neuregulin-1 isoforms HRG-α, HRG-α1A, HRG-α2B, HRG-α3, HRG-β1, HRG-β2, HRG-β3 (GGF), GGF2 and SMDF of mouse, rat and human origin by Western Blotting (starting dilution 1:200, dilution range 1:100-1:1000), immunoprecipitation [1-2 µg per 100-500 µg of total protein (1 ml of cell lysate)] and immunofluorescence (starting dilution 1:50, dilution range 1:50-1:500).

Secondary antibodies were:
Anti goat, HRP
sc-2922 Lot: C1405 Santa Cruz
Anti rabbit, HRP
Sc-2054 Lot: G 2005 Santa Cruz Next to immunostaining we performed MALDI-TOF and Q-TOF mass spectrometry to confirm NRG-1 beta-ECD.

Now we find a very similar pattern in APPPS mouse model of cerebral amyloidogenesis and Alzheimer's disease as shown in FIG. 8. The concentration of this particular acidic isoform of NRG-1 beta-ECD at roughly a pI of 5.0 is considerably higher in treated APPPS mice which are at the same time better learners.

In FIG. 8 two representative images are shown of each, a treated good learning animal (top) and non-treated animal with inferior learning performance. (below).

FIG. 9 shows the results of a Western Blot experiment using post mortem cortical material from each 9 Alzheimer patients and age-matched controls. It clearly reveals, that the NRG-1 β-ECD fragment is significantly less abundant in the Alzheimer cases. As an internal control the abundance of NRG-12 was measured, which appears not to be affected by the memory-loss associated with the disease.

A further investigation of the this specific Alzheimer- and memory-associated isoform of NRG-1 β-ECD by Western blots of 2-dimensional gels (2D-PAGE) of the same post mortem human brain material used for FIG. 9, reveals as shown by representative examples in FIG. 10, that it is indeed the acidic isoform of NRG-1β-ECD which is diminished in the Alzheimer condition.

CONCLUSIONS

We present here for the first time functional evidence of in vivo effects of posttranslational modifications of the transcript of nrg-1 gene, in particular a truncated form generated by proteolytic cleavage, comprising the extracellular domain of NRG-1 beta with MW 15-35, pI 4-10; more specifically we found an antipsychotic activity in animal models for schizophrenia, probably based on regulation of MAO-B and COMT, at concentrations of 5-600 ng/kg (i.v.). In contrast to control neuroleptics which are used at concentrations which are 100-1000-fold higher, there was no negative effect observed.

Moreover we found a neuroprotective effect in MPTP model of Parkinson's disease at concentrations of 3-300 ng/kg (i.v.)

Moreover we found a positive effect on memory- and learning in respective animal models (Morris water maze) for learning and cerebral amyloidosis and Alzheimer's disease Given the adverse effects of many atypical antipsychotics, currently in use (Haddad and Sharma 2007) we conclude that soluble NRG-1-ECD fragment with EGF domains of SMDF, NRG-1 alpha, but in particular NRG-1 beta might be useful as a stand-alone or co-medication for the treatment of schizophrenia, bipolar disorder and depression.

It might also be used in the same sense in other diseases of the central nervous system, like neurodegenerative disorders like Alzheimer's and Parkinson's disease, amyotrophic lateral sclerosis, multiple sclerosis, stroke, traumatic brain and spinal chord injuries.

Soluble NRG-1-ECD proteins have these very broad effects due to a central role in neuronal signal transduction, in particular mediating glutamate signalling and excitotoxicity, which plays a central role in all indications mentioned above (Schrattenholz and Soskic 2006).

REFERENCES

1. Arnold S E, Talbot K, Hahn C G (2005) Neurodevelopment, neuroplasticity, and new genes for schizophrenia. Prog Brain Res 147:319-345
2. Bao J, Lin H, Ouyang Y, Lei D, Osman A, Kim T W, Mei L, Dai P, Ohlemiller K K, Ambron R T (2004) Activity-dependent transcription regulation of PSD-95 by neuregulin-1 and Eos. Nat Neurosci 7:1250-1258
3. Benzel I, Bansal A, Browning B L, Galwey N W, Maycox P R, McGinnis R, Smart D, St C D, Yates P, Purvis I (2007) Interactions among genes in the ErbB-Neuregulin signalling network are associated with increased susceptibility to schizophrenia. Behav Brain Funct 3:31
4. Bertram I, Bernstein H G, Lendeckel U, Bukowska A, Dobrowolny H, Keilhoff G, Kanakis D, Mawrin C, Bielau H, Falkai P, Bogerts B (2007) Immunohistochemical evidence for impaired neuregulin-1 signaling in the prefrontal cortex in schizophrenia and in unipolar depression. Ann N Y Acad Sci 1096:147-156
5. Blackwood D H, Pickard B J, Thomson P A, Evans K L, Porteous D J, Muir W J (2007) Are some genetic risk factors common to schizophrenia, bipolar disorder and depression? Evidence from DISC1, GRIK4 and NRG1. Neurotox Res 11:73-83
6. Boissier J R, Simon P (1966) [On the potentiation of DOPA effects by monoamine oxidase inhibitors]. Psychopharmacologia 8:428-436
7. Britsch S (2007) The neuregulin-I/ErbB signaling system in development and disease. Adv Anat Embryol Cell Biol 190:1-65
8. Buonanno A, Fischbach G D (2001) Neuregulin and ErbB receptor signaling pathways in the nervous system. Curr Opin Neurobiol 11:287-296
9. Buresova O, Krekule I, Zahalka A, Bures J (1985) On-demand platform improves accuracy of the Morris water maze procedure. J Neurosci Methods 15:63-72
10. Costall B, Hui S C, Naylor R J (1978) Modulation of amphetamine hyperactivity by DPI injected into rat nucleus accumbens [proceedings]. Br J Pharmacol 64:461P
11. Eilam R, Pinkas-Kramarski R, Ratzkin B J, Segal M, Yarden Y (1998) Activity-dependent regulation of Neu differentiation factor/neuregulin expression in rat brain. Proc Natl Acad Sci USA 95:1888-1893
12. Esper R M, Pankonin M S, Loeb J A (2006) Neuregulins: versatile growth and differentiation factors in nervous system development and human disease. Brain Res Brain Res Rev 51:161-175
13. Falquet L, Pagni M, Bucher P, Hulo N, Sigrist C J, Hofmann K, Bairoch A (2002) The PROSITE database, its status in 2002. Nucleic Acids Res 30:235-238
14. Farmer A, Elkin A, McGuffin P (2007) The genetics of bipolar affective disorder. Curr Opin Psychiatry 20:8-12
15. Fischbach G D (2007) NRG1 and synaptic function in the CNS. Neuron 54:495-497
16. Geuna S, Nicolino S, Raimondo S, Gambarotta G, Battiston B, Tos P, Perroteau I (2007) Nerve regeneration along bioengineered scaffolds. Microsurgery 27:429-438
17. Glabe C (2006) Biomedicine. Avoiding collateral damage in Alzheimer's disease treatment. Science 314:602-603

18. Go R C, Perry R T, Wiener H, Bassett S S, Blacker D, Devlin B, Sweet R A (2005) Neuregulin-1 polymorphism in late onset Alzheimer's disease families with psychoses. Am J Med Genet B Neuropsychiatr Genet 139:28-32
19. Golub M S, Germann S L, Lloyd K C (2004) Behavioral characteristics of a nervous system-specific erbB4 knockout mouse. Behav Brain Res 153:159-170
20. Guo W P, Wang J, Li R X, Peng Y W (2006) Neuroprotective effects of neuregulin-1 in rat models of focal cerebral ischemia. Brain Res 1087:180-185
21. Haddad P M, Sharma S G (2007) Adverse effects of atypical antipsychotics: differential risk and clinical implications. CNS Drugs 21:911-936
22. Hahn C G, Wang H Y, Cho D S, Talbot K, Gur R E, Berrettini W H, Bakshi K, Kamins J, Borgmann-Winter K E, Siegel S J, Gallop R J, Arnold S E (2006) Altered neuregulin 1-erbB4 signaling contributes to NMDA receptor hypofunction in schizophrenia. Nat Med 12:824-828
23. Hanninen K, Katila H, Saarela M, Rontu R, Mattila K M, Fan M, Hurme M, Lehtimaki T (2007) Interleukin-1 beta gene polymorphism and its interactions with neuregulin-1 gene polymorphism are associated with schizophrenia. Eur Arch Psychiatry Clin Neurosci
24. Hoglinger G U, Breunig J J, Depboylu C, Rouaux C, Michel P P, varez-Fischer D, Boutillier A L, Degregori J, Oertel W H, Rakic P, Hirsch E C, Hunot S (2007) The pRb/E2F cell-cycle pathway mediates cell death in Parkinson's disease. Proc Natl Acad Sci USA 104:3585-3590
25. Hoglinger G U, Rizk P, Muriel M P, Duyckaerts C, Oertel W H, Caille I, Hirsch E C (2004) Dopamine depletion impairs precursor cell proliferation in Parkinson disease. Nat Neurosci 7:726-735
26. Holbro T, Hynes N E (2004) ErbB receptors: directing key signaling networks throughout life. Annu Rev Pharmacol Toxicol 44:195-217
27. Hong L E, Wonodi I, Stine O C, Mitchell B D, Thaker G K (2007) Evidence of Missense Mutations on the Neuregulin 1 Gene Affecting Function of Prepulse Inhibition. Biol Psychiatry
28. Hu X, Hicks C W, He W, Wong P, Macklin W B, Trapp B D, Yan R (2006) Bacel modulates myelination in the central and peripheral nervous system. Nat Neurosci 9:1520-1525
29. Karoutzou G, Emrich H M, Dietrich D E (2007) The myelin-pathogenesis puzzle in schizophrenia: a literature review. Mol Psychiatry
30. Kwon O B, Longart M, Vullhorst D, Hoffman D A, Buonanno A (2005) Neuregulin-1 reverses long-term potentiation at CA1 hippocampal synapses. J Neurosci 25:9378-9383
31. Li B, Woo R S, Mei L, Malinow R (2007) The neuregulin-1 receptor erbB4 controls glutamatergic synapse maturation and plasticity. Neuron 54:583-597
32. Liberatore G T, Jackson-Lewis V, Vukosavic S, Mandir A S, Vila M, McAuliffe W G, Dawson V L, Dawson T M, Przedborski S (1999) Inducible nitric oxide synthase stimulates dopaminergic neurodegeneration in the MPTP model of Parkinson disease. Nat Med 5:1403-1409
33. Mathew S V, Law A J, Lipska B K, vila-Garcia M I, Zamora E D, Mitkus S N, Vakkalanka R, Straub R E, Weinberger D R, Kleinman J E, Hyde T M (2007) {alpha}7 nicotinic acetylcholine receptor mRNA expression and binding in postmortem human brain are associated with genetic variation in Neuregulin 1. Hum Mol Genet
34. McIntosh A M, Moorhead T W, Job D, Lymer G K, Munoz M S, McKirdy J, Sussmann J E, Baig B J, Bastin M E, Porteous D, Evans K L, Johnstone E C, Lawrie S M, Hall J (2007) The effects of a neuregulin 1 variant on white matter density and integrity. Mol Psychiatry
35. Meeks T W, Ropacki S A, Jeste D V (2006) The neurobiology of neuropsychiatric syndromes in dementia. Curr Opin Psychiatry 19:581-586
36. Meyer-Luehmann M, Coomaraswamy J, Bolmont T, Kaeser S, Schaefer C, Kilger E, Neuenschwander A, Abramowski D, Frey P, Jaton A L, Vigouret J M, Paganetti P, Walsh D M, Mathews P M, Ghiso J, Staufenbiel M, Walker L C, Jucker M (2006) Exogenous induction of cerebral beta-amyloidogenesis is governed by agent and host. Science 313:1781-1784
37. Muller N, Schwarz M (2006) Schizophrenia as an inflammation-mediated dysbalance of glutamatergic neurotransmission. Neurotox Res 10:131-148
38. Nadri C, Belmaker R H, Agam G (2007) Oxygen restriction of neonate rats elevates neuregulin-1 alpha isoform levels: Possible relationship to schizophrenia. Neurochem Int 51:447-450
39. Owen M J, Craddock N, Jablensky A (2007) The genetic deconstruction of psychosis. Schizophr Bull 33:905-911
40. Ozaki M, Itoh K, Miyakawa Y, Kishida H, Hashikawa T (2004) Protein processing and releases of neuregulin-1 are regulated in an activity-dependent manner. J Neurochem 91:176-188
41. Ozaki M, Sasner M, Yano R, Lu H S, Buonanno A (1997) Neuregulin-beta induces expression of an NMDA-receptor subunit. Nature 390:691-694
42. Pertusa M, Morenilla-Palao C, Carteron C, Viana F, Cabedo H (2007) Transciptional control of cholesterol biosynthesis in Schwann cells by axonal neuregulin 1. J Biol Chem
43. Przedborski S, Vila M (2003) The 1-methyl-4-phenyl-1,2,3,6-tetrahydropyridine mouse model: a tool to explore the pathogenesis of Parkinson's disease. Ann N Y Acad Sci 991:189-198
44. Radde R, Bolmont T, Kaeser S A, Coomaraswamy J, Lindau D, Stoltze L, Calhoun M E, Jaggi F, Wolburg H, Gengler S, Haass C, Ghetti B, Czech C, Holscher C, Mathews P M, Jucker M (2006) Abeta42-driven cerebral amyloidosis in transgenic mice reveals early and robust pathology. EMBO Rep 7:940-946
45. Rimer M, Barrett D W, Maldonado M A, Vock V M, Gonzalez-Lima F (2005) Neuregulin-1 immunoglobulin-like domain mutant mice: clozapine sensitivity and impaired latent inhibition. Neuroreport 16:271-275
46. Ross C A, Margolis R L, Reading S A, Pletnikov M, Coyle J T (2006) Neurobiology of schizophrenia. Neuron 52:139-153
47. Schillo S, Pejovic V, Hunzinger C, Hansen T, Poznanovic S, Kriegsmann J, Schmidt W J, Schrattenholz A (2005b) Integrative proteomics: functional and molecular characterization of a particular glutamate-related neuregulin isoform. J Proteome Res 4:900-908
48. Schillo S, Pejovic V, Hunzinger C, Hansen T, Poznanovic S, Kriegsmann J, Schmidt W J, Schrattenholz A (2005a) Integrative proteomics: functional and molecular characterization of a particular glutamate-related neuregulin isoform. J Proteome Res 4:900-908
49. Schrattenholz A, Soskic V (2006) NMDA receptors are not alone: dynamic regulation of NMDA receptor structure and function by neuregulins and transient cholesterol-rich membrane domains leads to disease-specific nuances of glutamate-signalling. Curr Top Med Chem 6:663-686

50. Schubert C (2006) Alzheimer disease: BACE1 branches out. Nat Med 12:1123
51. Scolnick E M, Petryshen T, Sklar P (2006) Schizophrenia: do the genetics and neurobiology of neuregulin provide a pathogenesis model? Hary Rev Psychiatry 14:64-77
52. Thomson P A, Christoforou A, Morris S W, Adie E, Pickard B S, Porteous D J, Muir W J, Blackwood D H, Evans K L (2007) Association of Neuregulin 1 with schizophrenia and bipolar disorder in a second cohort from the Scottish population. Mol Psychiatry 12:94-104
53. Vila M, Przedborski S (2003) Targeting programmed cell death in neurodegenerative diseases. Nat Rev Neurosci 4:365-375
54. Willem M, Garratt A N, Novak B, Citron M, Kaufmann S, Ringer A, Destrooper B, Saftig P, Birchmeier C, Haass C (2006) Control of peripheral nerve myelination by the beta-secretase BACE1. Science 314:664-666
55. Woo R S, Li X M, Tao Y, Carpenter-Hyland E, Huang Y Z, Weber J, Neiswender H, Dong X P, Wu J, Gassmann M, Lai C, Xiong W C, Gao T M, Mei L (2007) Neuregulin-1 enhances depolarization-induced GABA release. Neuron 54:599-610
56. Xie F, Padival M, Siegel R E (2006) Association of PSD-95 with ErbB4 facilitates neuregulin signaling in cerebellar granule neurons in culture. J Neurochem
57. Xu Z, Croslan D R, Harris A E, Ford G D, Ford B D (2005a) Extended therapeutic window and functional recovery after intraarterial administration of neuregulin-1 after focal ischemic stroke. J Cereb Blood Flow Metab
58. Xu Z, Croslan D R, Harris A E, Ford G D, Ford B D (2006) Extended therapeutic window and functional recovery after intraarterial administration of neuregulin-1 after focal ischemic stroke. J Cereb Blood Flow Metab 26:527-535
59. Xu Z, Ford G D, Croslan D R, Jiang J, Gates A, Allen R, Ford B D (2005b) Neuroprotection by neuregulin-1 following focal stroke is associated with the attenuation of ischemia-induced pro-inflammatory and stress gene expression. Neurobiol Dis 19:461-470
60. Xu Z, Jiang J, Ford G, Ford B D (2004) Neuregulin-1 is neuroprotective and attenuates inflammatory responses induced by ischemic stroke. Biochem Biophys Res Commun 322:440-446
61. Yang X L, Huang Y Z, Xiong W C, Mei L (2005) Neuregulin-induced expression of the acetylcholine receptor requires endocytosis of ErbB receptors. Mol Cell Neurosci 28:335-346

The invention claimed is:

1. A method of treating a subject suffering from schizophrenia, comprising intravenously administering to the subject a recombinant soluble Type I Neuregulin-1 β isoform which is an about 15 to about 35 kD N-terminal fragment of Type I Neuregulin-1 β, wherein the recombinant soluble Type I Neuregulin-1 β isoform is the first 245, 246, 247, 248, 249, or 250 amino acids of Type I Neuregulin-1 β and is administered in an amount of about 400 ng/kg to about 600 ng/kg body weight of the subject to be treated.
2. The method of claim 1, wherein the recombinant soluble Type I Neuregulin-1 β isoform is the first 245 amino acids of Type I Neuregulin-1 β.
3. The method of claim 1, wherein the recombinant soluble Type I Neuregulin-1 β isoform crosses the blood-brain barrier.
4. The method of claim 1, wherein the recombinant soluble Type I Neuregulin-1 β isoform reduces dopaminergic cell death in the subject compared to a subject that is not treated with the recombinant soluble Type I Neuregulin-1 β isoform.
5. The method of claim 1, wherein the Type I Neuregulin-1 β isoform has an isoelectric point (pI) of about 4 to about 10.
6. The method of claim 1, wherein the Type I Neuregulin-1 β isoform is a modified polypeptide, wherein the modification is selected from phosphorylation, glycosylation, methylation, myristoylation, oxidation, and any combination thereof.
7. The method of claim 1, wherein the recombinant soluble Type I Neuregulin-1 β isoform is administered in an amount of 400 ng/kg to 600 ng/kg body weight of the subject to be treated.
8. The method of claim 1, wherein the recombinant soluble Type I Neuregulin-1 β isoform is administered in an amount of about 400 ng/kg body weight of the subject to be treated.
9. The method of claim 1, wherein the recombinant soluble Type I Neuregulin-1 β isoform is administered in an amount of about 600 ng/kg body weight of the subject to be treated.
10. The method of claim 1, wherein the recombinant soluble Type I Neuregulin-1 β isoform is administered in an amount of 400 ng/kg body weight of the subject to be treated.
11. The method of claim 1, wherein the recombinant soluble Type I Neuregulin-1 β isoform is administered in an amount of 600 ng/kg body weight of the subject to be treated.

* * * * *